(12) United States Patent
Sheldon et al.

(10) Patent No.: US 11,547,859 B2
(45) Date of Patent: Jan. 10, 2023

(54) IMPLANTABLE MEDICAL DEVICE AND METHOD FOR DETERMINING HIS BUNDLE PACING CAPTURE

(71) Applicant: Medtronic, Inc., Minneapolis, MN (US)

(72) Inventors: Todd J. Sheldon, North Oaks, MN (US); Elizabeth A. Mattson, Eagan, MN (US); Eric R. Williams, Maple Grove, MN (US); Zhongping Yang, Woodbury, MN (US); Shawn M. Campbell, Davidson, NC (US)

(73) Assignee: Medtronic, Inc., Minneapolis, MN (US)

( * ) Notice: Subject to any disclaimer, the term of this patent is extended or adjusted under 35 U.S.C. 154(b) by 64 days.

(21) Appl. No.: 17/321,828

(22) Filed: May 17, 2021

(65) Prior Publication Data

US 2021/0283402 A1 Sep. 16, 2021

Related U.S. Application Data

(63) Continuation of application No. 16/183,902, filed on Nov. 8, 2018, now Pat. No. 11,007,369.

(Continued)

(51) Int. Cl.
*A61N 1/37* (2006.01)
*A61N 1/378* (2006.01)
(Continued)

(52) U.S. Cl.
CPC .............. *A61N 1/371* (2013.01); *A61B 5/361* (2021.01); *A61B 5/363* (2021.01); *A61B 5/366* (2021.01); *A61B 5/4836* (2013.01); *A61B 5/686* (2013.01); *A61N 1/365* (2013.01); *A61N 1/3714* (2013.01); *A61N 1/3787* (2013.01); *A61N 1/37223* (2013.01); *A61N 1/37247* (2013.01); *A61N 1/3956* (2013.01); *A61B 5/283* (2021.01); *A61N 1/3756* (2013.01)

(58) Field of Classification Search
None
See application file for complete search history.

(56) References Cited

U.S. PATENT DOCUMENTS 4,505,276 A 3/1985 Markowitz et al.
6,148,234 A 11/2000 Struble
(Continued)

FOREIGN PATENT DOCUMENTS

EP 1234597 A2 8/2002

OTHER PUBLICATIONS

Adachi et al, "QRS Complex Widening Due to Loss of Left Bundle Branch Capture: Pitfail of Para-Hisian Pacing", Journal of Interventional Cardiac Electrophysiology 2009, 4 pages.

(Continued)

*Primary Examiner* — Ankit D Tejani

(57) ABSTRACT

An implantable medical device system receives a cardiac electrical signal produced by a patient's heart and comprising atrial P-waves and delivers a His bundle pacing pulse to the patient's heart via a His pacing electrode vector. The system determines a timing of a sensed atrial P-wave relative to the His bundle pacing pulse and determines a type of capture of the His bundle pacing pulse in response to the determined timing of the atrial P-wave.

21 Claims, 13 Drawing Sheets

Related U.S. Application Data

(60) Provisional application No. 62/663,619, filed on Apr. 27, 2018, provisional application No. 62/583,082, filed on Nov. 8, 2017.

(51) Int. Cl.

| | | |
|---|---|---|
| *A61N 1/39* | (2006.01) | |
| *A61N 1/372* | (2006.01) | |
| *A61B 5/00* | (2006.01) | |
| *A61N 1/365* | (2006.01) | |
| *A61B 5/361* | (2021.01) | |
| *A61B 5/363* | (2021.01) | |
| *A61B 5/366* | (2021.01) | |
| *A61N 1/375* | (2006.01) | |
| *A61B 5/283* | (2021.01) | |

(56) References Cited

U.S. PATENT DOCUMENTS

| | | |
|---|---|---|
| 6,408,210 B1 | 6/2002 | Bornzin et al. |
| 6,768,924 B2 | 7/2004 | Ding et al. |
| 8,155,741 B2 | 4/2012 | Bohn et al. |
| 8,565,880 B2 | 10/2013 | Dong et al. |
| 8,761,880 B2 | 6/2014 | Maskara et al. |
| 9,168,382 B2 | 10/2015 | Shuros et al. |
| 9,227,073 B2 | 1/2016 | Bohn et al. |
| 10,773,086 B2 | 9/2020 | Sheldon et al. |
| 2011/0264158 A1 | 10/2011 | Dong et al. |
| 2012/0101542 A1 | 4/2012 | Arcot-Krishnamurthy et al. |
| 2014/0018878 A1* | 1/2014 | Sathaye ............ A61N 1/365 607/25 |
| 2014/0107724 A1 | 4/2014 | Shuros et al. |
| 2015/0283385 A1* | 10/2015 | Sambelashvili ..... A61N 1/3627 607/18 |
| 2017/0232261 A1 | 8/2017 | Stadler et al. |
| 2019/0192860 A1 | 6/2019 | Ghosh et al. |

OTHER PUBLICATIONS

Deshmukh et al., "Permanent, Direct HIS-Bundle Pacing: A Novel Approach to Cardiac Pacing in Patients with Normal HIS-Purkinje Activation", Circulation, American Heart Association, Inc., vol. 101, No. 8, Feb. 29, 2000, 9 pages.

Dandamudi et al., "How to Perform Permanent His Bundle Pacing in Routine Clinical Practice", 2016, Heart Rhythm Society, 5 pages.

Yuyun et al., "HIS Bundle Pacing: State of the Art", US Cardiology, vol. 12, No. 1, Jan. 2017, 10 pages.

(PCT/US2018/059766) PCT Notification of Transmittal of the International Search Report and the Written Opinion of the International Searching Authority, dated Jan. 24, 2019, 14 pages.

(PCT/US2018/059770) PCT Notification of Transmittal of the International Search Report and the Written Opinion of the International Searching Authority, dated Feb. 11, 2019, 13 pages.

* cited by examiner

IMPLANTABLE MEDICAL DEVICE AND METHOD FOR DETERMINING HIS BUNDLE PACING CAPTURE

REFERENCE TO RELATED APPLICATIONS

This application is a Continuation of U.S. patent application Ser. No. 16/183,902, filed on Nov. 8, 2018, which claims the benefit of U.S. Patent Application No. 62/583,082, filed provisionally on Nov. 8, 2017, and the benefit of U.S. Patent Application No. 62/663,619, filed provisionally on Apr. 27, 2018, all of which are incorporated herein by reference in their entirety.

TECHNICAL FIELD

This disclosure relates to an implantable medical device and method for determining a type of cardiac capture produced by a His bundle pacing pulse delivered to a patient's heart.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (AV) node. The AV node responds by propagating a ventricular depolarization signal through the bundle of His of the ventricular septum and thereafter to the bundle branches and the Purkinje muscle fibers of the right and left ventricles.

Patients with a conduction system abnormality, e.g., poor AV node conduction or poor SA node function, may receive a pacemaker to restore a more normal heart rhythm and AV synchrony. Ventricular pacing may be performed to maintain the ventricular rate in a patient having atrioventricular conduction abnormalities. A single chamber ventricular pacemaker may be coupled to a transvenous ventricular lead carrying electrodes placed in the right ventricle, e.g., in the right ventricular apex. The pacemaker itself is generally implanted in a subcutaneous pocket with the transvenous lead tunneled to the subcutaneous pocket. Intracardiac pacemakers have been introduced or proposed for implantation entirely within a patient's heart, eliminating the need for transvenous leads. An intracardiac pacemaker may provide sensing and pacing from within a chamber of the patient's heart, e.g., from within the right ventricle in a patient having AV conduction block.

Dual chamber pacemakers are available which include a transvenous atrial lead carrying electrodes which are placed in the right atrium and a transvenous ventricular lead carrying electrodes that are placed in the right ventricle via the right atrium. A dual chamber pacemaker senses atrial electrical signals and ventricular electrical signals and can provide both atrial pacing and ventricular pacing as needed to promote a normal atrial and ventricular rhythm and restore AV synchrony when both SA and/or AV node or other conduction abnormalities are present.

Cardiac pacing of the His bundle has been proposed to provide ventricular pacing along the heart's natural conduction system. Ventricular pacing at the right ventricular apex has been found to be associated with increased risk of atrial fibrillation and heart failure. Alternative pacing sites have been investigated or proposed, such as pacing of the His bundle. Pacing the ventricles via the His bundle allows recruitment along the heart's natural conduction system, including the Purkinje fibers, and is hypothesized to promote more physiologically normal electrical and mechanical synchrony than other pacing sites, such as the ventricular apex.

SUMMARY

The techniques of this disclosure generally relate to determining the type of capture achieved by cardiac pacing pulses delivered via His bundle pacing electrodes. Among the types of capture that may be achieved during His bundle pacing are selective His bundle capture, non-selective His bundle capture, ventricular myocardial capture, atrial capture, and loss of ventricular capture. The type of capture may depend on the location of the electrodes relative to the His bundle, the pacing pulse energy and other factors. An implantable medical device (IMD) operating according to the techniques disclosed herein may determine the type of capture following a His bundle pacing pulse for determining various capture thresholds for use in selecting pacing pulse control parameters and for monitoring capture during His bundle pacing to detect a change in capture type.

In one example, the disclosure provides an IMD system including a sensing circuit, a therapy delivery circuit and a control circuit coupled to the sensing circuit and the therapy delivery circuit. The sensing circuit is configured to receive a cardiac electrical signal produced by a patient's heart and comprising atrial P-waves. The therapy delivery circuit is configured to generate His bundle pacing pulses delivered to a patient's heart via a His pacing electrode vector. The control circuit is configured to control the therapy delivery circuit to deliver a His bundle pacing pulse, determine the timing of an atrial P-wave sensed by the sensing circuit relative to the delivered His bundle pacing pulse, and determine a type of capture of the His bundle pacing pulse in response to the determined timing of the atrial P-wave.

In another example, the disclosure provides a method performed by an IMD. The method includes receiving a cardiac electrical signal produced by a patient's heart and comprising atrial P-waves and delivering a His bundle pacing pulse to the patient's heart via a His pacing electrode vector. The method further includes determining by a control circuit of the implantable medical device the timing of an atrial P-wave sensed by the sensing circuit relative to the His bundle pacing pulse and determining a type of capture of the His bundle pacing pulse in response to the determined timing of the atrial P-wave.

In yet another example, the disclosure provides a non-transitory, computer-readable storage medium comprising a set of instructions which, when executed by a control circuit of an IMD, cause the IMD to receive a cardiac electrical signal produced by a patient's heart and comprising atrial P-waves, deliver a His bundle pacing pulse to the patient's heart via a His pacing electrode vector, determine the timing of an atrial P-wave sensed by the sensing circuit relative to the His bundle pacing pulse, and determine a type of capture of the His bundle pacing pulse in response to the determined timing of the atrial P-wave.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

An IMD capable of delivering His bundle pacing and detecting and monitoring capture of the His bundle is described herein. A heart chamber is "captured" by a pacing pulse having sufficient electrical energy to cause depolarization of the cardiac tissue, causing an electrical "evoked response," and subsequent mechanical contraction of the heart chamber. In order to effectively capture and pace the heart to achieve a desired therapeutic effect, cardiac pacing pulses need to have a pulse energy that is equal to or greater than the capture threshold of the cardiac tissue at the pacing site. A pacing capture threshold test may be performed to determine the minimum pacing pulse amplitude for a given pacing pulse width (or vice versa) that captures the heart chamber. Determination of the capture threshold enables proper programming of the pacing pulse amplitude and pulse width to promote effective pacing and avoid loss of capture. Capture monitoring by the pacemaker allows automatic adjustments to the pacing pulse amplitude and/or width to a suprathreshold value when loss of capture is detected.

When pacing pulses are delivered by electrodes positioned in the heart to pace the His bundle, it is possible to capture only the His bundle tissue, capture both the His bundle and surrounding ventricular myocardium, or capture the surrounding ventricular myocardium without capturing the His bundle. Capture of only the His bundle is referred to herein as "selective" His bundle (SHB) capture. Capture of the His bundle and surrounding ventricular myocardial tissue is referred to herein as "non-selective" His bundle (NSHB) capture. Capture of the surrounding ventricular myocardium without capturing the His bundle is referred to as ventricular myocardial (VM) capture. In some instances, other types of capture may occur in response to an intended His bundle pacing pulse such as capture of only the right bundle branch, atrial capture instead of His bundle or VM capture, or fusion when a His bundle pacing pulse capture and an intrinsic depolarization occur simultaneously. Determination of which type of capture is occurring in response to an intended His bundle pacing pulse and determination of the His bundle capture threshold allows for providing selective or non-selective pacing of the His bundle in order to achieve pacing along the native ventricular conduction system.

Figure 1:
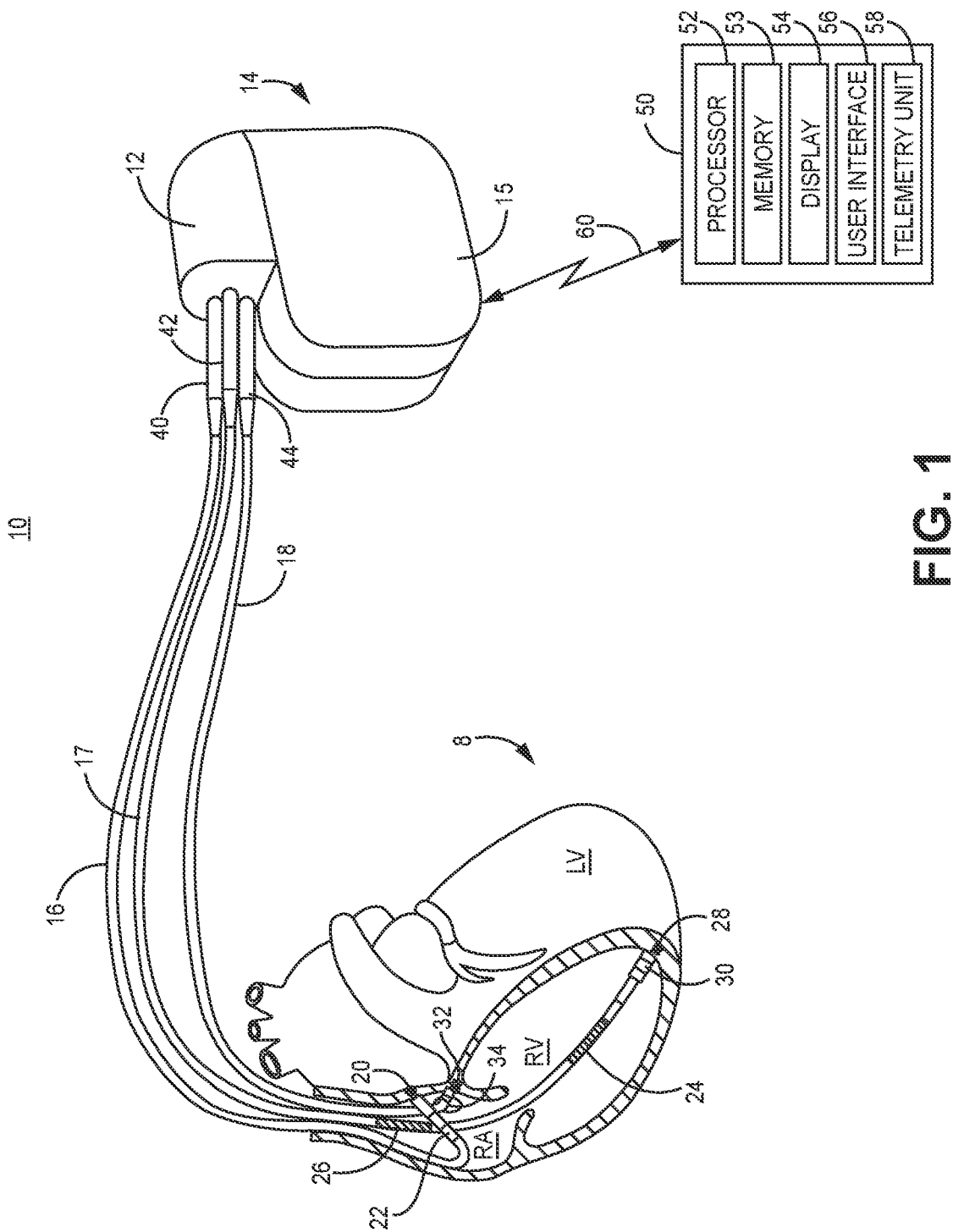
FIG. 1 is a conceptual diagram of an IMD system capable of pacing and sensing in a patient's heart.

FIG. 1 is a conceptual diagram of an IMD system 10 capable of pacing and sensing in a patient's heart 8. The IMD system 10 includes IMD 14 coupled to a patient's heart 8 via transvenous electrical leads 16, 17 and 18. IMD 14 is shown as a dual chamber device capable of delivering cardiac pacing pulses and sensing cardiac electrical signals in the right atrium (RA) and in the right ventricle (RV). Housing 15 encloses internal circuitry corresponding to the various circuits and components described in conjunction with FIG. 3 below, for sensing cardiac signals from heart 8, detecting arrhythmias, controlling therapy delivery and monitoring His bundle capture using the techniques disclosed herein.

IMD 14 includes a connector block 12 that may be configured to receive the proximal ends of a RA lead 16, RV lead 17 and a His lead 18, which are advanced transvenously for positioning electrodes for sensing and stimulation in the RA and RV. RA lead 16 is positioned such that its distal end is in the vicinity of the right atrium and the superior vena cava. RA lead 16 is equipped with pacing and sensing electrodes 20 and 22, shown as a tip electrode 20 and a ring electrode 22 spaced proximally from tip electrode 20. The electrodes 20 and 22 provide sensing and pacing in the right atrium and are each connected to a respective insulated conductor extending within the elongated body of RA lead 16. Each insulated conductor is coupled at its proximal end to a connector carried by proximal lead connector 40.

His lead 18 is advanced within the right atrium to position electrodes 32 and 34 for pacing and sensing in the vicinity of the His bundle. His lead tip electrode 32 may be a helical electrode that is advanced into the inferior end of the interatrial septum, beneath the AV node and near the tricuspid valve annulus to position tip electrode 32 in or proximate to the His bundle. A ring electrode 34 spaced proximally from tip electrode 32 may be used as the return electrode with the cathode tip electrode 32 for pacing the right and left ventricles via the native ventricular conduction system extending from the His bundle. An intracardiac electrogram (EGM) signal may be produced by IMD 14 from the cardiac electrical signal obtained using the tip electrode 32 and ring electrode 34 of His lead 18 and received by sensing circuitry included in IMD 14. As described below, the EGM signal produced from the cardiac electrical signal received via His lead 18 may be used for detecting capture of the His bundle and discriminating between SHB capture, NSHB capture, VM capture and loss of capture. The electrodes 32 and 34 are coupled to respective insulated conductors extending within the elongated body of His lead 18, which provide electrical connection to the proximal lead connector 44 coupled to connector block 12.

In some examples, IMD 14 may optionally be coupled to RV lead 17 for positioning electrodes within the RV for sensing RV cardiac signals and delivering pacing or shocking pulses in the RV. For these purposes, RV lead 17 is equipped with pacing and sensing electrodes shown as a tip electrode 28 and a ring electrode 30. RV lead 17 is further shown to carry defibrillation electrodes 24 and 26, which may be elongated coil electrodes used to deliver high voltage CV/DF pulses. Defibrillation electrode 24 may be referred to as the "RV defibrillation electrode" or "RV coil electrode" because it may be carried along RV lead 17 such that it is positioned substantially within the right ventricle when distal pacing and sensing electrodes 28 and 30 are positioned for pacing and sensing in the right ventricle. Defibrillation electrode 26 may be referred to as a "superior vena cava (SVC) defibrillation electrode" or "SVC coil electrode" because it may be carried along RV lead 17 such that it is positioned at least partially along the SVC when the distal end of RV lead 17 is advanced within the right ventricle.

Each of electrodes 24, 26, 28 and 30 are connected to a respective insulated conductor extending within the body of RV lead 17. The proximal end of the insulated conductors are coupled to corresponding connectors carried by proximal lead connector 42, e.g., a DF-4 connector, for providing electrical connection to IMD 14. In other examples, RV lead 17 may carry RV coil electrode 24 and SVC coil electrode 26 to provide high voltage therapies without carrying any pacing and sensing electrodes 28 and 30. Housing 15 may function as an active electrode during CV/DF shock delivery in conjunction with RV coil electrode 24 or SVC coil electrode 26. In some examples, housing 15 may function as a return electrode for unipolar sensing or pacing configurations with any of the electrodes carried by leads 16, 17 and 18.

It is to be understood that although IMD 14 is illustrated in FIG. 1 as an implantable cardioverter defibrillator capable of delivering both low voltage cardiac pacing therapies and high voltage cardioversion and defibrillation (CV/DF) shocks, IMD 14 may be configured as a dual-chamber pacemaker in other examples coupled to only RA lead 16 and His lead 18 without having CV/DF shock delivery capabilities and without being coupled to a third lead, such as RV lead 17. In still other examples, IMD 14 may be a single chamber device coupled only to His lead 18 for delivering pacing pulses to the ventricles for at least maintaining a minimum ventricular rate.

An external device 50 is shown in telemetric communication with IMD 14 by a communication link 60. External device 50 may include a processor 52, memory 53, display unit 54, user interface 56 and telemetry unit 58. Processor 52 controls external device operations and processes data and signals received from IMD 14. Display unit 54, which may include a graphical user interface, displays data and other information to a user for reviewing 1 MB operation and programmed parameters as well as cardiac electrical signals retrieved from IMD 14. Data obtained from IMD 14 via communication link 60 may be displayed on display unit 54. For example, a clinician may view cardiac electrical signals received from IMD 14 and/or results of His capture threshold testing and monitoring or data derived therefrom.

User interface 56 may include a mouse, touch screen, key pad or the like to enable a user to interact with external device 50 to initiate a telemetry session with IMD 14 for retrieving data from and/or transmitting data to IMD 14, including programmable parameters for controlling His capture determination as described herein. Telemetry unit 58 includes a transceiver and antenna configured for bidirectional communication with a telemetry circuit included in IMD 14 and is configured to operate in conjunction with processor 52 for sending and receiving data relating to ICD functions via communication link 60, which may include data relating to His bundle and ventricular capture management, such as capture thresholds determined for SHB capture, NSHB capture, VM capture.

Communication link 60 may be established between 1 MB 14 and external device 50 using a radio frequency (RF) link such as BLUETOOTH®, Wi-Fi, or Medical Implant Communication Service (MICS) or other RF or communication frequency bandwidth or communication protocols. Data stored or acquired by IMD 14, including physiological signals or associated data derived therefrom, results of device diagnostics, and histories of detected rhythm episodes and delivered therapies, may be retrieved from IMD 14 by external device 50 following an interrogation command.

External device 50 may be embodied as a programmer used in a hospital, clinic or physician's office to retrieve data from 1 MB 14 and to program operating parameters and algorithms in 1 MB 14 for controlling 1 MB functions. External device 50 may alternatively be embodied as a home monitor or hand held device. External device 50 may be used to program cardiac signal sensing parameters, cardiac rhythm detection parameters and therapy control parameters used by IMD 14. Thresholds or other parameters used for detecting SHB capture, NSHB capture and VM capture according to techniques disclosed herein may be programmed into IMD 14 using external device 50.

Figure 2:
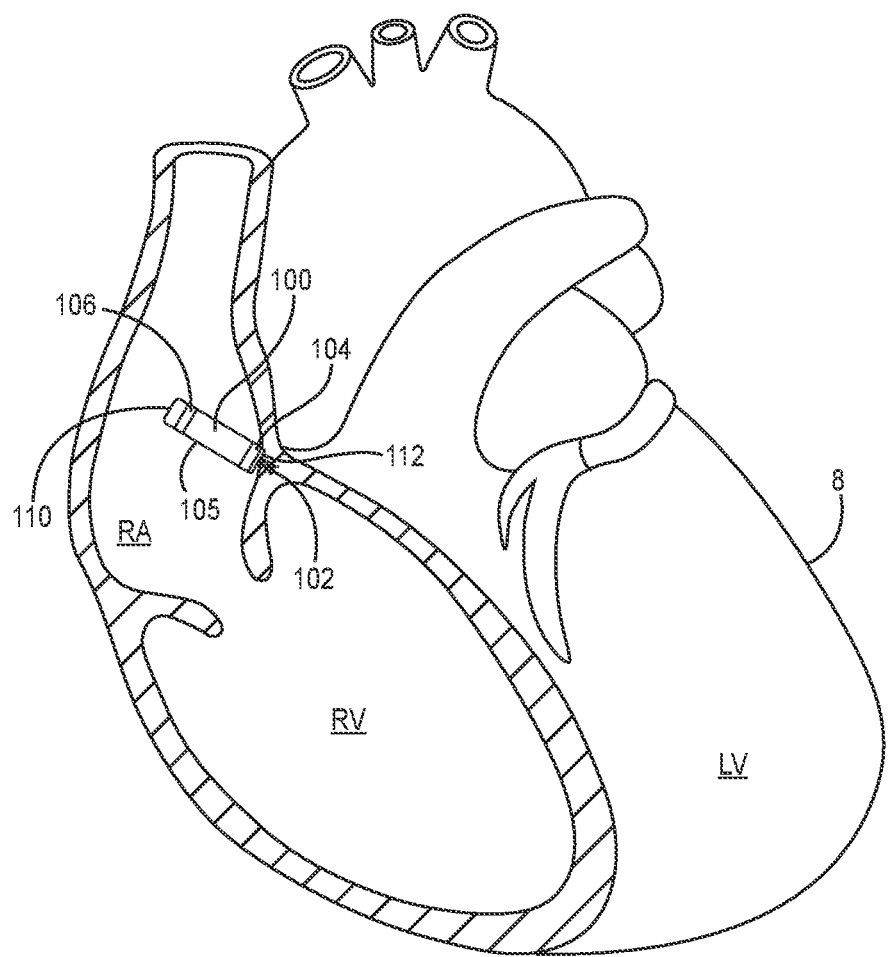
FIG. 2 is a conceptual diagram of a leadless intracardiac pacemaker positioned within the right atrium for providing ventricular pacing.

FIG. 2 is a conceptual diagram of a leadless intracardiac pacemaker 100 positioned within the RA of a patient's heart 8 for providing ventricular pacing via the His bundle. Pacemaker 100 may include a distal tip electrode 102 extending away from a distal end 112 of the pacemaker housing 105. Intracardiac pacemaker 100 is shown implanted in the RA of the patient's heart 8 to place distal tip electrode 102 for delivering pacing pulses to the His bundle. For example, the distal tip electrode 102 may be inserted into the inferior end of the interatrial septum, beneath the AV node and near the tricuspid valve annulus to position tip electrode 102 in, along or proximate to the His bundle. Distal tip electrode 102 may be a helical electrode providing fixation to anchor the pacemaker 100 at the implant position. In other examples, pacemaker 100 may include a fixation member that includes one or more tines, hooks, barbs, helices or other fixation member(s) that anchor the distal end of the pacemaker 100 at the implant site.

A portion of the distal tip electrode 102 may be electrically insulated such that only the most distal end of tip electrode 102, furthest from housing distal end 112, is exposed to provide targeted pacing at a tissue site that includes a portion of the His bundle. One or more housing-based electrodes 104 and 106 may be carried on the surface of the housing of pacemaker 100. Pacing of the His bundle may be achieved using the distal tip electrode 102 as the cathode electrode and either of the housing-based electrodes 104 and 106 as the return anode.

Cardiac electrical signals produced by heart 8 may be sensed by pacemaker 100 using a sensing electrode pair selected from electrodes 102, 104 and 106. For example, a near-field signal may be sensed using distal tip electrode 112 and distal housing-based electrode 104. A second electrical signal, which is a relatively more far-field signal, may be sensed using electrodes 104 and 106. The cardiac electrical signals may be analyzed for determining His bundle capture and discriminating between at least SHB capture, NSHB capture and VM capture.

Figure 3:
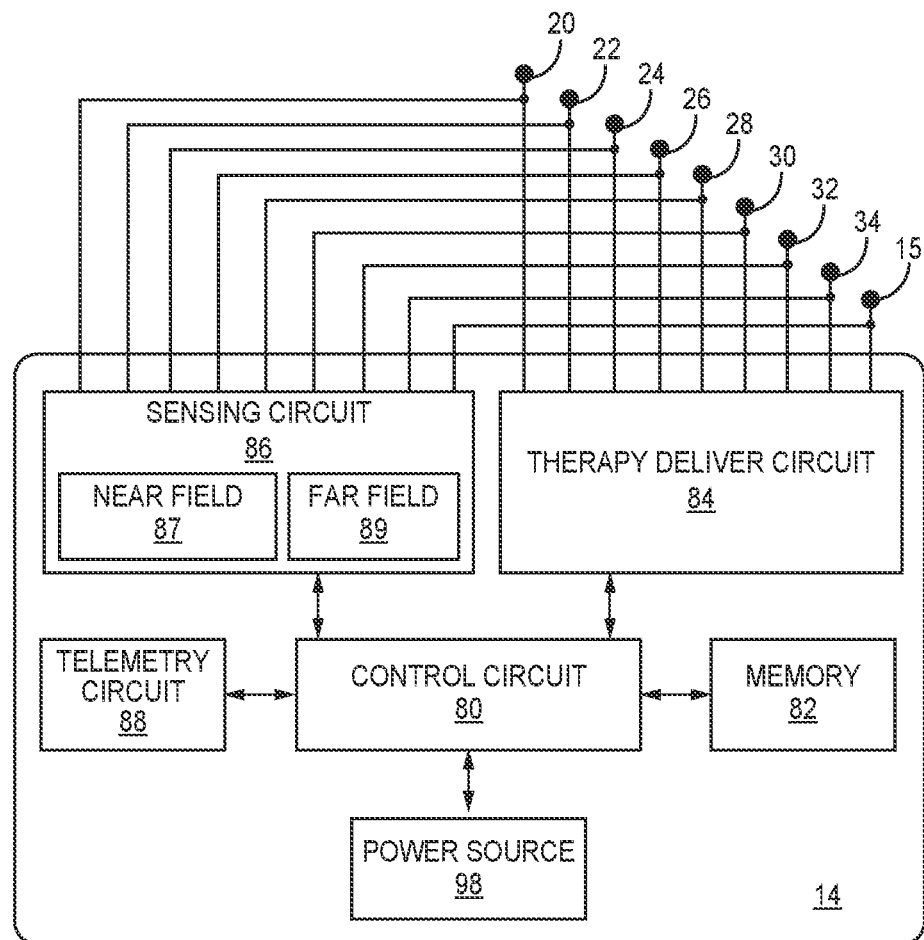
FIG. 3 is a schematic diagram of circuitry that may be enclosed within an IMD configured to perform His bundle pacing and capture detection.

FIG. 3 is a schematic diagram of circuitry that may be enclosed within an IMD configured to perform His bundle pacing and capture detection. The block diagram of FIG. 3 represents IMD 14 for the sake of illustration but it is to be understood that the functionality attributed to the various circuits and components shown in FIG. 3 for performing His bundle pacing and detection and discrimination of SHB, NSHB and VM capture among other types of capture and/or loss of capture may be similarly implemented in the intracardiac pacemaker 100 of FIG. 2 or other IMDs capable of delivering His pacing pulses and sensing cardiac electrical signals. Housing 15 is represented as an electrode in FIG. 3 for use in sensing and electrical stimulation pulse delivery. The electronic circuitry enclosed within housing 15 includes software, firmware and hardware that cooperatively monitor cardiac electrical signals, determine when a pacing therapy is necessary, and deliver electrical pacing pulses to the patient's heart as needed according to programmed pacing mode and pacing pulse control parameters. The electronic circuitry includes a control circuit 80, memory 82, therapy delivery circuit 84, sensing circuit 86, telemetry circuit 88 and power source 98.

Power source 98 provides power to the circuitry of IMD 14 including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86, and 88 are to be understood from the general block diagram of FIG. 3, but are not all shown for the sake of clarity. For example, power source 98 may be coupled to one or more charging circuits included in therapy delivery circuit 84 for providing the power needed to charge holding capacitors included in therapy delivery circuit 84 that are discharged at appropriate times under the control of control circuit 80 for delivering pacing pulses. Power source 98 is also coupled to components of sensing circuit 86, such as sense amplifiers, analog-to-digital converters, switching circuitry, etc., telemetry circuit 88 and memory 82 to provide power to the various circuits as needed.

The functional blocks shown in FIG. 3 represent functionality included in IMD 14 and may include any discrete and/or integrated electronic circuit components that implement analog and/or digital circuits capable of producing the functions attributed to IMD 14 (or pacemaker 100) herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. Providing software, hardware, and/or firmware to accomplish the described functionality in the context of any modern cardiac medical device system, given the disclosure herein, is within the abilities of one of skill in the art.

Control circuit 80 communicates, e.g., via a data bus, with therapy delivery circuit 84 and sensing circuit 86 for sensing cardiac electrical signals and controlling delivery of cardiac electrical stimulation therapies in response to sensed cardiac events, e.g., P-waves and R-waves, or the absence thereof. The available electrodes are electrically coupled to therapy delivery circuit 84 for delivering electrical stimulation pulses to the patient's heart and/or to sensing circuit 86 for sensing cardiac electrical signals produced by the heart, including both intrinsic signals produced by the heart in the absence of a stimulation pulse and evoked response signals produced by the heart in response to a delivered stimulation pulse.

Sensing circuit 86 may include two or more sensing channels for sensing cardiac electrical signals from two or more sensing electrode vectors. For example, a RA signal may be sensed using electrodes 20 and 22, an RV signal may be sensed using electrodes 28 and 30, and a His signal may be sensed using electrodes 32 and 34. As described below, a His bundle near field signal may be sensed by one sensing channel, shown as near field sensing channel 87, for example using electrodes 32 and 34 of His lead 18. A far field signal may be sensed by a second sensing channel, shown as far field sensing channel 89.

As used herein, a "near field" signal refers to a cardiac electrical signal received from a sensing electrode vector including at least one electrode positioned in or proximate to the His bundle, in the vicinity of the site of His pacing pulse delivery, such that the near field signal may also be referred to as a "His bundle near field signal." The His bundle near field signal may or may not include a His bundle evoked response depending on whether the His bundle was captured or not. In various instances, the His bundle near field signal may include an evoked response signal caused by SHB capture, an evoked response signal caused by NSHB capture or an evoked response signal caused by VM capture.

As used herein, a "far field" signal refers to a cardiac electrical signal received from a sensing electrode vector that is relatively further away from the His bundle than the electrode vector used to sense the His bundle near field signal and/or has a greater inter-electrode distance between the two electrodes defining the far field sensing electrode vector than the inter-electrode distance of the near field sensing electrode vector. The far field signal is more representative of the global activation of the ventricles as opposed to the near field signal, which is more representative of local tissue activation at or near the pacing site. The far field signal may include an evoked response signal associated with SHB capture, NSHB capture or VM capture. When the His bundle is captured, either selectively or non-selectively, the far field QRS width is narrower than when the His bundle is not captured and the ventricular myocardial tissue is captured instead.

In some examples, the far field signal may be sensed using an electrode carried by RA lead 16 and the IMD housing 15, e.g., electrode 20 and housing 15 or electrode 22 and housing 15. In examples that include RV lead 17, the far field signal may be sensed using RV coil electrode 24 paired with housing 15, SVC coil electrode 26 paired with housing 15, or RV coil electrode 24 paired with SVC coil electrode 26. The His bundle capture detection methods disclosed herein include, in some examples, detecting SHB capture from the near field signal and discriminating between NSHB capture and VM capture from the far field signal when SHB capture is not detected.

Sensing circuit 86 may include switching circuitry for selectively coupling a near field sensing electrode pair from the available electrodes to the near field sensing channel 87 for sensing a near field His bundle signal and for selectively coupling a far field sensing electrode pair to far field sensing channel 89 for sensing an electrical signal that is far field relative to the site of delivering His bundle pacing pulses. The far field sensing electrode pair may exclude at least one or both of the electrodes used to deliver the His bundle pacing pulses. Switching circuitry may include a switch array, switch matrix, multiplexer, or any other type of switching device suitable to selectively couple components of sensing circuit 86 to selected electrodes.

Each of near field sensing channel 87 and far field sensing channel 89 may include an input filter for receiving a cardiac electrical signal from a respective sensing electrode pair, a pre-amplifier, an analog-to-digital converter and a bandpass filter for producing a multi-bit digital EGM signal for use in detecting His bundle capture and discriminating between at least SHB, NSHB, and VM capture and may discriminate between other types of capture, such as right bundle branch capture, and fusion. Features of the near field and far field EGM signals may be determined by control circuit 80, and in some examples each sensing channel 87 and 89 may include a rectifier to produce a rectified signal from which signal features may be determined by control circuit 80 for use in determining His bundle capture. As described below in conjunction with FIGS. 4-6, the QRS signal following a His bundle pacing pulse may be used to detect His bundle pacing pulse capture and discriminate between different types of capture based upon features of the QRS signal in the near field and far field signals. The QRS signal following a His bundle pacing pulse that captures the His bundle and/or the ventricular myocardium may also be referred to herein as an "evoked response signal" and includes the evoked response R-wave that may be sensed by sensing circuit 86.

Sensing circuit 86 may include cardiac event detection circuitry, which may include one or more sense amplifiers, filters, rectifiers, threshold detectors, comparators, analog-to-digital converters (ADCs), timers or other analog or digital components, for detecting cardiac electrical events. A cardiac event sensing threshold, such as a P-wave sensing threshold or an R-wave sensing threshold, may be automatically adjusted by sensing circuit 86 under the control of control circuit 80, e.g., based on timing intervals and sensing threshold values determined by control circuit 80, stored in memory 82, and/or controlled by hardware, firmware and/or software of control circuit 80 and/or sensing circuit 86. For example, an atrial event detector may be included in sensing circuit 86 for detecting P-waves attendant to atrial depolarizations using one or both of electrodes 20 and 22 carried by RA lead 16. A sensed P-wave may be an intrinsic P-wave or a retrograde conducted P-wave arising from capture of the ventricular myocardium and/or His bundle. As described in conjunction with FIGS. 11-13, the timing of a sensed P-wave may be used in detecting retrograde conduction due to capture of the His bundle or VM capture outside the physiological refractory period of the atrial myocardium. The timing of a sensed P-wave relative to a His bundle pacing pulse is different depending on the capture type and therefore may be used in some examples to discriminate between capture types of the His bundle pacing pulse delivered asynchronously with the atrial rhythm.

A ventricular event detector may be included in sensing circuit 86 for detecting intrinsic R-waves attendant to intrinsic ventricular depolarizations using electrodes 32 and 34 carried by His lead 18 and/or using electrodes 24, 26, 28 and/or 30 carried by RV lead 17. Upon detecting a cardiac electrical event based on a sensing threshold crossing, sensing circuit 86 may produce a sensed event signal that is passed to control circuit 80. For example, an atrial event detector may produce a P-wave sensed event signal in response to a P-wave sensing threshold crossing. A ventricular event detector may produce an R-wave sensed event signal in response to an R-wave sensing threshold crossing. The sensed event signals are used by control circuit 80 for setting pacing escape interval timers that control the basic time intervals used for scheduling cardiac pacing pulses. Control circuit 80 may include various timers or counters for counting down an atrioventricular (AV) pacing interval, a VV pacing interval, an AA pacing interval, etc. A sensed event signal may trigger or inhibit a pacing pulse depending on the particular programmed pacing mode. For example, a P-wave sensed event signal received from sensing circuit 86 may cause control circuit 80 to inhibit a scheduled atrial pacing pulse and schedule a His bundle pacing pulse at the programmed AV pacing interval. If the AV pacing interval expires before control circuit 80 receives an R-wave sensed event signal from sensing circuit 86, control circuit 80 may control therapy delivery circuit 84 to deliver a His pacing pulse at the AV pacing interval following the sensed P-wave and in this way deliver atrial-synchronized ventricular pacing. If an R-wave sensed event signal is received from sensing circuit 86 before the AV pacing interval expires, the scheduled His pacing pulse may be inhibited. The AV pacing interval controls the amount of time between an atrial event, paced or sensed, and a His bundle pacing pulse to promote AV synchrony.

Therapy delivery circuit 84 may include charging circuitry, one or more charge storage devices such as one or more holding capacitors, an output capacitor, and switching circuitry that controls when the holding capacitor(s) are charged and discharged across the output capacitor to deliver a pacing pulse to a selected pacing electrode vector coupled to therapy delivery circuit 84. Therapy delivery circuit 84 may include one or more pacing channels. In the example of 1 MB 14, therapy delivery circuit 84 may include an RA pacing channel, a His pacing channel and an RV pacing channel each including a holding capacitor, one or more switches, and an output capacitor for producing pacing pulses delivered by the respective RA lead 16, RV lead 17 and His lead 18. Charging of a holding capacitor to a programmed pacing voltage amplitude and discharging of the capacitor for a programmed pacing pulse width may be performed by therapy delivery circuit 84 according to control signals received from control circuit 80. For example, a pace timing circuit included in control circuit 80 may include programmable digital counters set by a microprocessor of the control circuit 80 for controlling the basic pacing time intervals associated with various single chamber or dual chamber pacing modes or anti-tachycardia pacing sequences. The microprocessor of control circuit 80 may also set the amplitude, pulse width, polarity or other characteristics of the cardiac pacing pulses, which may be based on programmed values stored in memory 82.

In some examples, IMD 14 may be configured to detect non-sinus tachycardia and deliver anti-tachycardia pacing (ATP). Control circuit 80 may determine cardiac event time intervals, e.g., PP intervals between consecutive P-wave sensed event signals received from sensing circuit 86 and RR intervals between consecutive R-wave sensed event signals received from sensing circuit 86. These intervals may be compared to tachycardia detection intervals for detecting non-sinus tachycardia. Tachycardia may be detected in a given heart chamber based on a threshold number of tachycardia detection intervals being detected. In response to detecting atrial or ventricular tachycardia, control circuit 80 may control therapy delivery circuit 84 to deliver ATP.

Therapy delivery circuit 84 may include high voltage therapy circuitry for generating high voltage shock pulses in addition to low voltage therapy circuitry for generating relatively lower voltage pacing pulses. In response to detecting atrial or ventricular tachycardia or fibrillation, control circuit 80 may control therapy delivery circuit 84 to deliver a cardioversion/defibrillation (CV/DF) shock. The high voltage therapy circuitry may include high voltage capacitors and associated charging circuitry for generating and delivering CV/DF shock pulses using coil electrodes 24 and 26 and/or housing 15.

Control parameters utilized by control circuit 80 for sensing cardiac events, and controlling pacing therapy delivery may be programmed into memory 82 via telemetry circuit 88. Telemetry circuit 88 includes a transceiver and antenna for communicating with an external device 50 (FIG. 1) using radio frequency communication or other communication protocols. Under the control of control circuit 80, telemetry circuit 88 may receive downlink telemetry from and send uplink telemetry to the external device 50. In some cases, telemetry circuit 88 may be used to transmit and receive communication signals to/from another medical device implanted in the patient.

Figure 4:
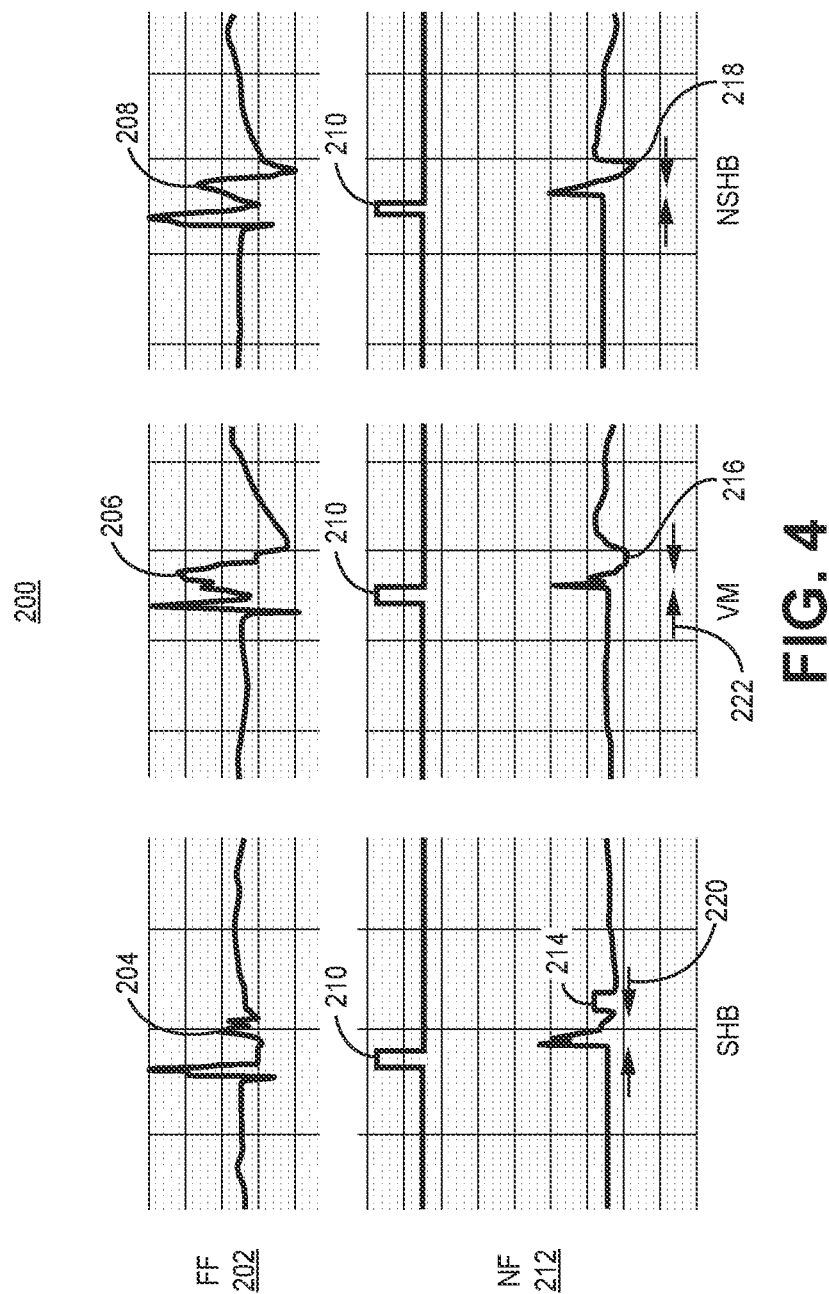
FIG. 4 is a diagram of evoked response signals representing different types of cardiac capture in response to His bundle pacing pulses.

FIG. 4 is a diagram 200 of cardiac electrical signals including evoked response signals representing SHB capture (left column), NSHB capture (right column), and VM capture (center column). Far field cardiac electrical signals 202 and corresponding His bundle near field signals 212 are shown aligned in time with a respective His bundle pacing pulse 210 in each example.

In the left column, the His bundle pacing pulse 210 that results in SHB capture produces a His bundle near field evoked response signal 214 that occurs after a time delay 220 from the His pacing pulse 210. The His bundle near field evoked response signal 214 has a positive polarity and relatively narrow signal width. The far field evoked response signal 204 is also seen to be relatively narrow, positive in polarity and occurring after a time delay. The time delay 220 following the His bundle pacing pulse 210 until the QRS complex (evoked response signal 214) is due to the time required for the depolarization to be conducted along the His Purkinje conduction system.

In the middle column, the far field evoked response signal 206 and the corresponding His bundle near field evoked response signal 216 following a His bundle pacing pulse 210 that only captures ventricular myocardial tissue without capturing the His bundle are shown. The near field evoked response signal 216 occurs after a relatively shorter time delay 222 than the time delay 220 of evoked response signal 214 during SHB capture due to the absence of conduction along the His Purkinje conduction system. The near field evoked response signal 216 during VM capture is relatively wide and has a negative polarity.

The far field evoked response signal 208 and His bundle near field evoked response signal 218 during NSHB capture are shown in the right column. In the His bundle near field signal 212, the VM capture evoked response signal 216 (middle column) and the NSHB evoked response signal 218 are substantially similar. Both signals 216 and 218 occur early after the respective His bundle pacing pulse 210, both are negative in polarity and have similar signal widths, which are relatively wider than the SHB evoked response signal 214. Accordingly, SHB capture may be positively detected from the His bundle near field signal 212, e.g., based on the longer time delay 220 until the evoked response signal 214, the positive polarity (at least in some patients), a relatively narrow signal width, a relatively small signal waveform area or any combination thereof. The similarities of the timing and morphology of the His bundle near field evoked response signal 218 during NSHB capture and the near field evoked response signal 216 during VM capture may make these two types of capture difficult to distinguish from the His bundle near field signal 212 alone.

The far field evoked response signal 208 during NSHB capture, however, is distinctly narrower than the far field evoked response signal 206 during VM capture. If SHB capture is not positively detected based on a late, narrow and/or positive polarity of near field evoked response signal 214, the type of capture, e.g., either VM capture or NSHB capture, may be determined from a far field signal 202, e.g., based on the far field evoked response signal width, area, and/or QRS waveform morphology. A QRS width, area or waveform template for a known type of capture may be established or determined. For instance, a wavelet transform may be performed on the QRS waveform of an unknown type of capture to produce wavelet coefficients that are compared to wavelet coefficients of a known capture template. Known capture templates may be generated for SHB capture, NSHB capture and/or VM capture. A template comparison to an unknown QRS waveform may be used to determine the capture type during His pacing capture monitoring. A QRS template comparison of either the His bundle near field and/or far field signal may be performed alone or in combination with comparisons of the QRS width and/or QRS area to respective thresholds for determining the type of capture achieved by a His bundle pacing pulse.

Figure 5:
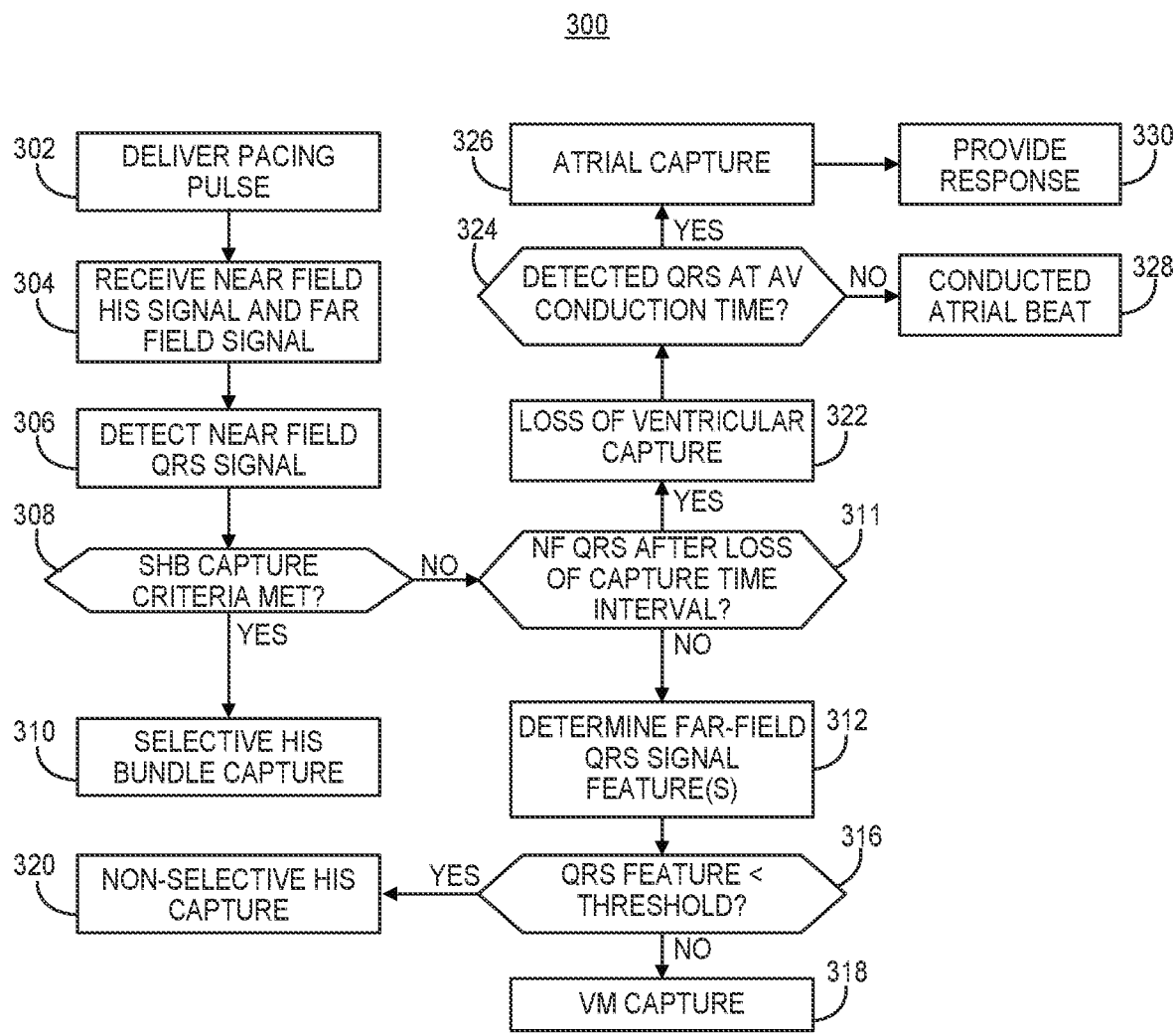
FIG. 5 is a flow chart of a method for determining a type of cardiac capture following a His bundle pacing pulse.

FIG. 5 is a flow chart 300 of a method, which may be performed by IMD 14 or intracardiac pacemaker 100, for determining a type of cardiac capture following a His bundle pacing pulse. At block 302, the control circuit 80 controls therapy delivery circuit 84 to generate and deliver a His bundle pacing pulse. The His bundle pacing pulse may be delivered using a His lead, e.g., electrodes 32 and 34 of His lead 18 in the example of IMD 14 of FIG. 1. The His bundle pacing pulse may be delivered by an intracardiac pacemaker, e.g., using electrodes 102 and 104 of intracardiac pacemaker 100 of FIG. 2.

At block 304, a His bundle near field signal and a far field cardiac electrical signal are received by sensing circuit 86. The His bundle near field signal may be received by the same electrodes used for delivering the His bundle pacing pulse, e.g., tip electrode 32 and ring electrode 34 (FIG. 1). In other examples, at least one electrode used for delivering the His bundle pacing pulse is used for sensing the His bundle near field signal, e.g., using the tip electrode 32 and housing 15. By using tip electrode 32, e.g., paired with the IMD housing 15, the evoked response to a His bundle pacing pulse that captures ventricular myocardial tissue will be conducted away from the pacing tip electrode 32 resulting in a greater likelihood of a negative polarity of the evoked QRS signal during VM capture and NSHB capture. The polarity of the evoked QRS signal when SHB capture occurs is expected to be positive. The polarity of the evoked QRS signal sensed during SHB capture, NSHB capture and VM capture using a selected near field sensing electrode vector may be established at the time of implant or follow up testing to verify that the polarity of the signal is a distinguishing feature between SHB capture (positive polarity) and other types of capture that includes ventricular myocardial tissue (NSHB and VM capture).

In the example of IMD 14 of FIG. 1, the far field signal may be received by a sensing electrode that excludes the electrodes used for delivering the His bundle pacing pulse. For instance, using the example of FIG. 1, the far field signal may be received using RA tip electrode 20 and housing 15, RA ring electrode 22 and housing 15, RV coil electrode 24 and housing 15, SVC coil electrode 26 and housing 15, RV tip electrode 28 and housing 15, or RV ring electrode 30 and housing 15. In other examples, RA tip electrode 20, RA ring electrode 22, RV tip electrode 28 or RV ring electrode 30 may be used in combination with either of RV coil electrode 24 or SVC coil electrode 26 to obtain a far field cardiac electrical signal. In the example of intracardiac pacemaker 100 of FIG. 2, the far field cardiac electrical signal may be received using housing based electrodes 104 and 106, for example.

At block 306, the control circuit 80 detects the QRS signal following the delivered His bundle pacing pulse in the near field signal. In some examples, the near field QRS signal is detected by sensing circuit 86 based on a threshold crossing of the near field signal. A QRS detection signal may be passed to control circuit 80 from near field channel 87. In other examples, control circuit 80 may receive a digital near field signal from sensing circuit 86 and determine the time of the QRS signal based on a threshold crossing, slew rate or other feature of the near field evoked response signal.

The control circuit 80 may compare the near field QRS signal to SHB capture criteria at block 308. The control circuit 80 may determine that SHB capture criteria are met by the near field QRS signal at block 308 in response to the time interval from the delivered His bundle pacing pulse to the time of the detected near field QRS signal being greater than an SHB time interval threshold but less than a loss of capture time interval threshold. For example, the time interval 220 from the His bundle pacing pulse to the time of detecting the near field QRS signal may be determined by the control circuit 80 and compared to a time interval threshold. The SHB time interval threshold may be set to at least 30 ms, at least 40 ms, or at least 50 ms in various examples and may be programmable for tailoring to an individual patient. A QRS signal detected earlier than the SHB time interval threshold is an indication of capture of myocardial cells and may be NSHB capture or VM capture.

In some instances, the His bundle pacing pulse may fail to capture both the His bundle and ventricular myocardial tissue, resulting in no ventricular evoked response following the His pacing pulse. A QRS signal may still occur, however, due to a conducted atrial beat, intrinsic or paced, if AV conduction is intact. The atrial depolarization may be conducted to the ventricles but may occur at a prolonged delay after the His bundle pacing pulse that failed to capture the ventricles. As such, the near field SHB capture criteria applied at block 308 may require that the QRS signal be detected within a time interval range, after a SHB time interval threshold but not later than a loss of capture time interval threshold.

The SHB capture criteria applied to the near field QRS signal at block 308 may require that the near field QRS signal be detected after the SHB time interval threshold (and before a loss of capture time interval threshold), be a positive polarity signal, have a signal width less than a threshold width, have a signal area less than a threshold area, or any combination thereof. If the near field QRS signal satisfies the SHB capture criteria at block 308, the control circuit 80 detects SHB capture at block 310.

In response to the near field QRS signal not meeting the SHB capture criteria at block 308, e.g., the QRS signal occurs earlier than the SHB threshold time interval, has a negative polarity, a signal width greater than a threshold width, and/or a signal area greater than a threshold area, SHB capture is not detected. The process advances to block 311. If the NF QRS signal is detected after the loss of capture time interval threshold, control circuit 80 may detect loss of ventricular capture at block 322. The delivered His bundle pacing pulse may fail to capture both the His bundle and the ventricular myocardial tissue. The His pacing pulse may fail to capture both the His bundle and the ventricular myocardium but may capture atrial myocardium in some instances causing an atrial depolarization. If AV conduction is intact, the atrial depolarization may be conducted to the ventricles, and the resulting QRS signal may be detected from the His bundle near field signal. However, the QRS signal conducted from the atria in this situation occurs at a prolonged delay, e.g., corresponding to the AV conduction time, and is evidence of loss of capture of the ventricles by the His pacing pulse. As such, loss of ventricular capture may be detected at block 322.

In some examples, the time from the His bundle pacing pulse to the detected QRS signal may be compared to an expected AV conduction time at block 324 in response to detecting loss of ventricular capture at block 322. Atrial capture may be suspected if the QRS signal is detected after a loss of capture time interval threshold and within a predetermined range of an approximate or expected AV conduction time required for an atrial depolarization to be conducted to the ventricles via the AV node. Atrial capture may be determined at block 326. If the QRS signal is detected at a time interval after the His bundle pacing pulse that is not within a range of an expected AV conduction time, an intrinsic atrial beat or an evoked atrial depolarization caused by an atrial pacing pulse, e.g., delivered by RA electrodes 20 and 22 of FIG. 1, may have been conducted to the ventricles. The detected QRS signal may be determined to be a conducted atrial beat at block 328.

If atrial capture is determined at block 326, an atrial capture response may be provided by control circuit 80 at block 330. The response may include reporting atrial capture by storing the event in memory 82 and transmitting a report of atrial capture to external device 50, generating an alert or alarm to the patient and/or clinician to notify the clinician that atrial capture is occurring and follow up is needed, and/or adjust His bundle pacing pulse control parameters or switch to ventricular pacing via a different pacing electrode vector, e.g., using electrodes carried by an RV lead 17 if present. In some cases, adjusting the pacing pulse amplitude, pacing pulse width, AV pacing interval, or other His bundle pacing control parameter may preclude atrial capture and enable His bundle and/or VM capture.

While not explicitly shown in FIG. 5, it is to be understood that if no QRS signal is detected at block 306 before a VV pacing interval expires, a backup His bundle pacing pulse may be delivered, e.g., at an increased pacing pulse energy. Control circuit 80 may set a VV pacing interval to provide backup ventricular pacing to prevent ventricular asystole, e.g., in a patient with complete AV block. In the example of FIG. 1, a backup ventricular pacing pulse may be provided by electrodes carried by RV lead 17.

If the SHB capture criteria are not met, and the detected QRS signal is not later than the loss of capture time interval threshold ("no" branch of block 311), control circuit 80 may analyze the far field QRS signal at block 312 to determine if the QRS signal corresponds to a different type of capture. Control circuit 80 may receive a digitized far field signal from far field sensing channel 89 and determine one or more features of the far field QRS signal. One or more features of the far field QRS signal are compared to criteria for discriminating between NSHB capture and VM capture. For example, the far field QRS signal width and/or the QRS signal area may be determined at block 312. The evoked response signal during VM capture and the evoked response signal during NSHB capture may both occur relatively early after the His bundle pacing pulse and have the same polarity in both of the near field and far field signals. In the far field signal, however, the NSHB capture evoked response signal is expected to have a narrower signal width and/or smaller signal area than the VM capture evoked response signal.

Accordingly, at block 316, one or more far field QRS signal features are compared to NSHB capture criteria. The far field QRS signal width may be determined and compared to a NSHB width threshold and/or the far field QRS signal area may be determined and compared to a NSHB area threshold. If one or both of the far field QRS signal width and the far field QRS signal area are less than the respective width or area threshold, NSHB capture is detected at block 320. If the far field QRS signal feature(s) do not meet the NSHB capture criteria applied at block 316, VM capture is detected at block 318.

After determining the type of capture or determining loss of capture (e.g., at one of blocks 310, 318, 320, 322, 326 or 328) control circuit 80 may return to block 302 to continue monitoring the His bundle near field electrical signal and a far field cardiac electrical signal for providing capture monitoring on a beat-by beat or less frequent basis. In other examples, the process of FIG. 5 may be performed during a His bundle capture threshold test. Various examples of the applications of the capture determination methods of FIG. 5 are described below in conjunction with FIGS. 7-10.

Figure 6:
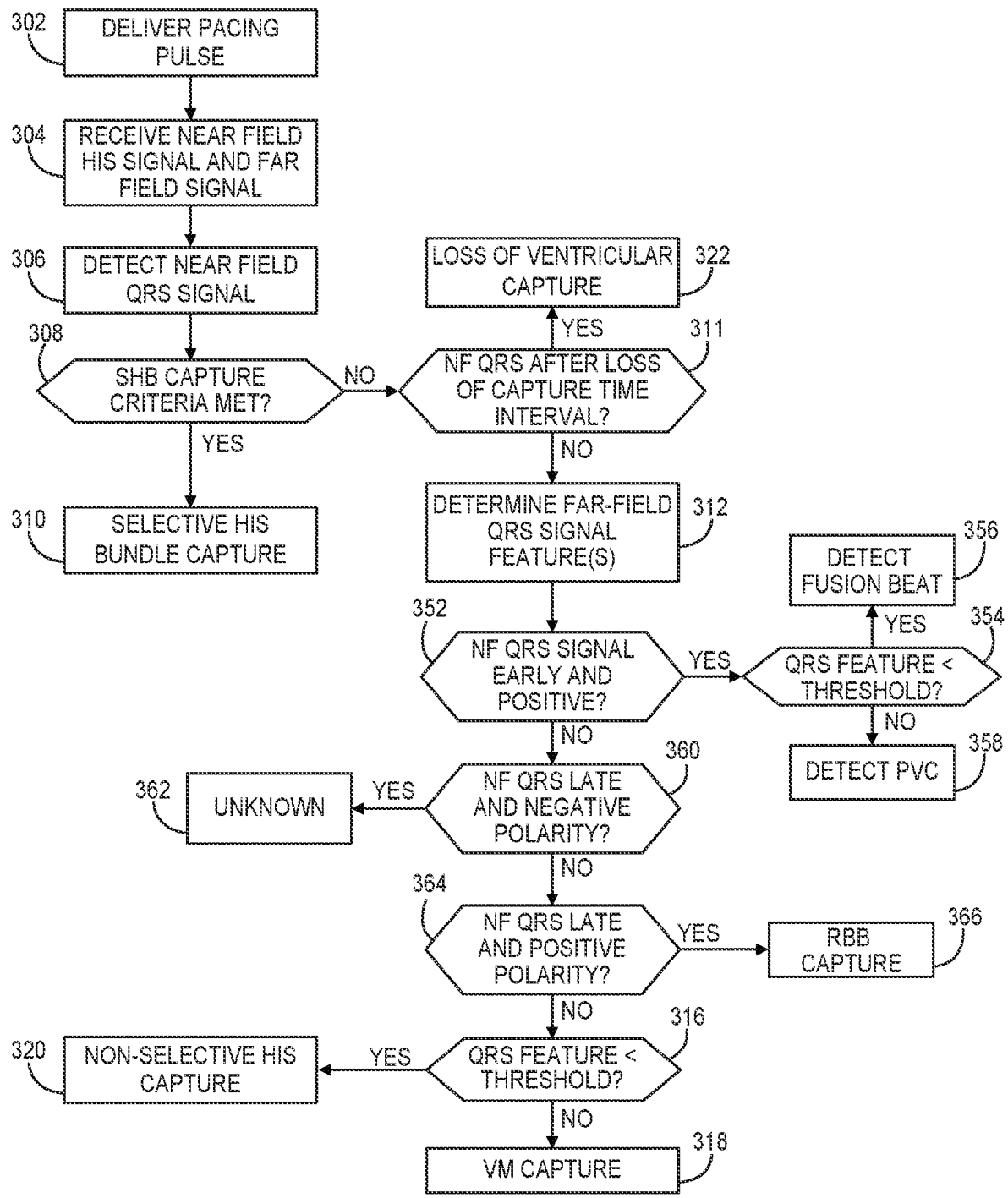
FIG. 6 is a flow chart of a method performed by an IMD for discriminating between different types of capture, loss of capture and other events following a His bundle pacing pulse according to another example.

FIG. 6 is a flow chart 350 of a method performed by an 1 MB for discriminating between different types of capture according to another example. In some cases, some but not all of the SHB capture criteria applied at block 308 of FIG. 5 may be satisfied. For example, the QRS signal may have a positive polarity but occur earlier than the SHB time interval threshold. In other instances, the QRS signal may be detected after the SHB time interval threshold but have a negative polarity. In such cases, SHB capture is not determined but the criteria for detecting NSHB capture criteria (e.g., a negative polarity QRS signal before the SHB time interval threshold and a narrow far field QRS signal width) or the VM capture criteria (e.g., a negative polarity QRS signal that occurs before the SHB time interval threshold and a wide far field QRS signal width) may not be satisfied either since some but not all SHB capture criteria were met. In these cases, the QRS signal may correspond to a fusion beat, a premature ventricular contraction (PVC), or selective capture of a bundle branch, e.g., the right bundle branch (RBB) without capturing the left bundle branch (LBB).

In the example of FIG. 6, additional criteria may be applied to the near field QRS signal and/or the far field QRS signal for discriminating between other types of capture or detecting other types of events. Identically numbered blocks in FIG. 6 correspond to like-numbered blocks shown in FIG. 5 and described above. If the SHB capture criteria are not met at block 308 and the near field QRS signal is not after the loss of capture time interval threshold ("no" branch of block 311), the QRS signal feature(s) are determined from the far field signal at block 312 as described above.

Decision blocks 352, 360 and 364 take into account situations when one of the SHB criteria are satisfied but not all. For example, if the near field QRS signal has a positive polarity but occurs early after the His bundle pacing pulse rather than after the SHB time interval threshold ("yes" branch of block 352), the QRS signal may represent a fusion beat or a PVC. A fusion beat and a PVC may be discriminated by comparing the far field QRS signal width and/or area at block 354. If the determined far field QRS signal width or area is greater than a respective width or area threshold, the early, positive polarity NF QRS signal is detected as a PVC at block 358. If the early, positive polarity NF QRS signal has a signal width and/or area that is less than the respective width or area threshold, a fusion beat is detected at block 356.

At block 360, control circuit 80 may account for the situation of the near field QRS signal being late, after the SHB time interval threshold but before the loss of capture time interval threshold, suggesting SHB capture but having a negative polarity instead of the expected positive polarity if SHB capture has occurred. If the near field QRS signal is after the SHB time interval threshold but has a negative polarity, the beat may be determined to be an unknown beat at block 362.

If the near field QRS signal is detected late, after the SHB time interval threshold but before the loss of capture time interval threshold, and has a positive polarity but didn't meet QRS signal width and/or area criteria for detecting SHB capture at block 308 ("yes" branch of block 364), right bundle branch capture (RBB capture) may be detected at block 366. In this case, a wide QRS signal is not consistent with SHB capture but a late occurring, positive QRS signal suggests the ventricular conduction system was captured by the His pacing pulse. Capture of the RBB causes the late, positive polarity NF QRS and the wide QRS signal (or large QRS area) is evidence of conduction from the right to the left ventricle that takes longer than when the His bundle is captured and the depolarization is conducted to both the right and left bundle branches.

If the detected near field QRS signal is both early, before the SHB time interval threshold, and negative in polarity, the far field QRS signal feature(s) determined at block 312 (e.g., signal width and/or area) may be compared to a threshold at block 316 for discriminating between NSHB capture and VM capture as described above in conjunction with FIG. 5.

The techniques of FIGS. 5 and 6 for detecting a QRS signal following a His bundle pacing pulse and discriminating between at least SHB capture, NSHB capture, VM capture, and loss of capture (which may include determining atrial capture) may be used during a pacing capture threshold test, during capture monitoring during His bundle pacing, and/or during an IMD implant procedure for verifying acceptable electrode placement. Determination of the capture type following a QRS signal enables selection of pacing pulse parameters for achieving the desired capture type as further described below.

FIGS. 5 and 6 illustrate particular examples of criteria that may be applied for detecting different types of cardiac capture, loss of capture or other events from the near field His bundle electrical signal and the far field electrical signal. In Table I, an example truth table is shown listing example characteristics of the near field (NF) QRS signal and the far field (FF) QRS width that may be used to define criteria for detecting a variety of capture types and other events following a His bundle pacing pulse by analyzing the His bundle near field signal and the far field cardiac electrical signal. Based on these criteria, a variety of algorithms may be developed for detecting and discriminating different types of capture and other events that may occur following a His bundle pacing pulse. "Early" and "late" NF QRS time as listed in Table I may be defined as before or after, respectively, the SHB time interval threshold. "Very late" NF QRS time may be a QRS signal sensed after the loss of capture time interval threshold. "Narrow" and "wide" FF QRS width as listed in Table I may be defined as less than or greater than, respectively, a QRS width threshold. The actual criteria listed in Table I may vary between particular 1 MB systems and between patients, e.g., depending on 1 MB and electrode locations and other factors. The algorithms based on truth table criteria may include evaluating a feature of the His bundle near field signal to detect SHB capture followed by evaluating one or more features of the far field signal for determining the capture type if SHB capture is not detected.

TABLE I

Example "truth" table for establishing criteria for determining capture type and detecting loss of ventricular (LOV) capture and other events based on the NF QRS time (from the delivered His bundle pacing pulse), the NF QRS signal polarity, and the FF QRS signal width.

| EVENT | NF QRS time | NF QRS polarity | FF QRS width |
|---|---|---|---|
| NSHB capture | Early | negative | narrow |
| SHB capture | Late | positive | narrow |
| Fusion beat | Early | positive | narrow |
| PVC | Early | positive | wide |
| Unknown | Late | negative | narrow or wide |
| VM capture | Early | negative | wide |
| RBB capture | Late | positive | wide |
| LOV capture | very late | either | either |

Figure 7:
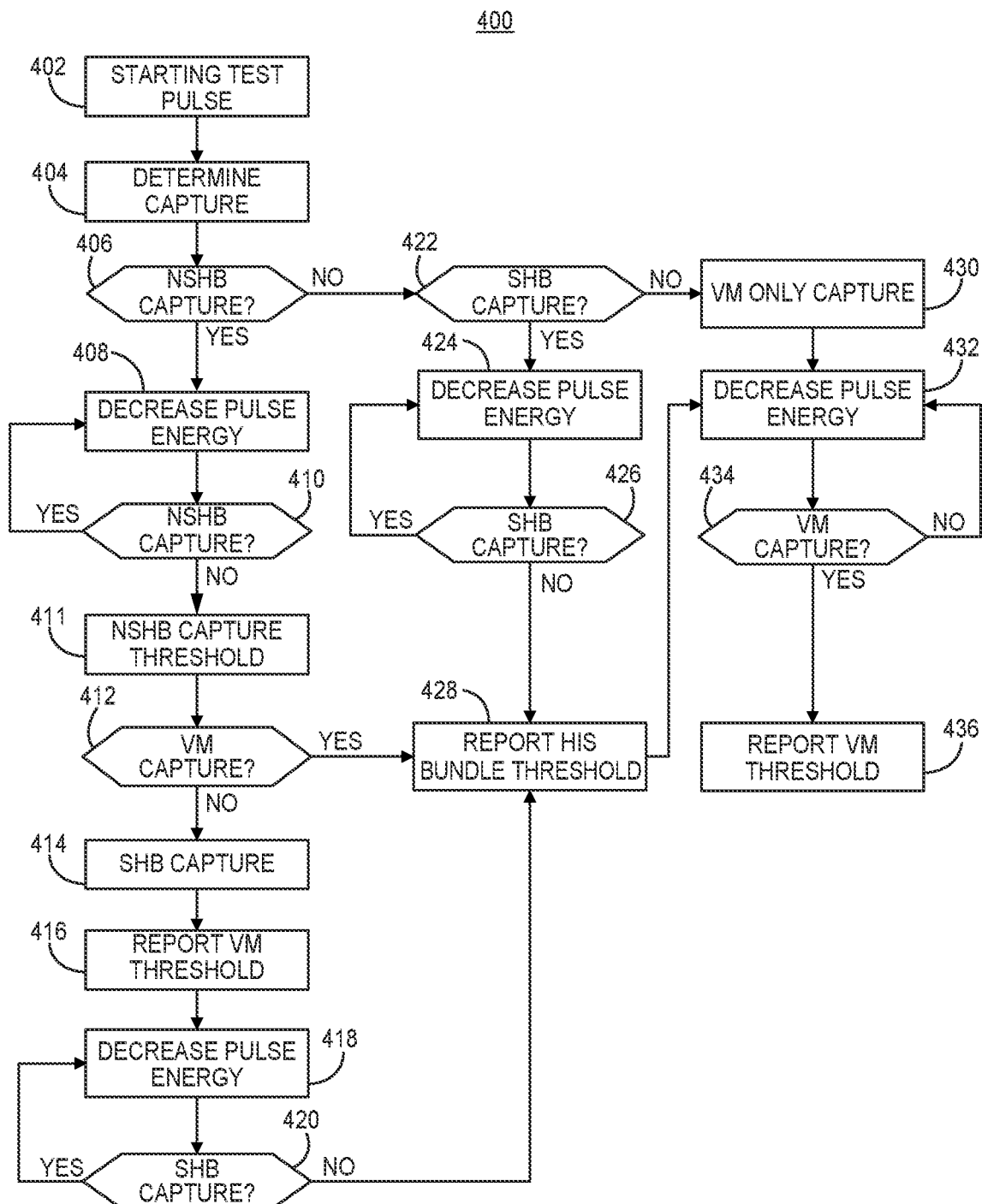
FIG. 7 is a flow chart for performing a capture threshold test for His bundle pacing according to one example.

FIG. 7 is a flow chart 400 for performing a threshold test for His bundle pacing according to one example. At block 402, the capture threshold test is started by delivering a His bundle pacing pulse at a test amplitude and test pulse width using a selected His bundle pacing electrode vector. The starting pacing pulse amplitude may be, with no limitation intended, up to 5.0 Volts, and the starting pulse width may be 0.4 ms or up to 1 ms. At block 404, capture is determined. The capture threshold test may be started with a relatively high pacing pulse energy such that ventricular capture is expected. It is to be understood that if loss of ventricular capture is detected, as described in conjunction with FIG. 5, the pulse energy may be increased to a higher starting test pulse energy.

In the example shown in FIG. 7, assuming ventricular capture occurs in response to the starting test pulse, ventricular capture is shown as being determined as one of SHB capture (block 422), NSHB capture (block 406), or VM capture (block 430). It is recognized however, that the additional criteria for detecting other types of capture or events, e.g., a fusion beat, PVC, RBB capture or an unknown signal, may be applied at block 404 in other examples. If a fusion beat, PVC, or unknown signal is detected at block 404, delivery of the starting test pulse may be repeated, possibly at a different pacing interval to avoid fusion and promote capture of the His bundle and/or the ventricular myocardium.

Capture may be determined at block 404 by analyzing both the His bundle near field signal and the far field cardiac electrical signal according to the techniques described above in conjunction with FIG. 5. In other examples, control circuit 80 may initially analyze the far field cardiac electrical signal to determine if NSHB capture is detected. For example, NSHB capture may be detected based on the far field signal evoked response signal occurring before the SHB time interval threshold and having a QRS signal width less than a width threshold and/or signal area that is less than an area threshold. NSHB capture may be further confirmed by analyzing the His bundle near field signal to verify that SHB capture detection criteria are not met.

If NSHB capture is detected as determined at decision block 406, control circuit 80 may be configured to automatically decrease the His bundle pacing pulse energy in a stepwise manner to determine the His bundle capture threshold and the VM capture threshold. The His bundle capture threshold may be greater than the VM capture threshold in some patients, and in other patients the VM capture threshold may be greater than the His bundle capture threshold.

The His bundle capture threshold and the VM capture threshold may change over time in a given patient, for example, due changes in tissue encapsulation of the pacing electrode vector and/or or shifts in electrode location. As such, at one time the His bundle capture threshold may be higher than the VM capture threshold in a given patient, and at another time the VM capture threshold may be higher than the His bundle capture threshold. Accordingly, the threshold test of FIG. 7 may be performed to determine the two separate His bundle capture threshold and VM capture threshold. The higher one of the His bundle capture threshold and the VM capture threshold is also the NSHB capture threshold since both the His bundle and the ventricular myocardial tissue are being captured at the higher capture threshold.

At block 408, the pulse energy is decreased, for instance, by decreasing the pulse amplitude by 1.0 Volts, 0.5 Volts, 0.25 Volts, or other predetermined decrement. In other examples, the pacing pulse amplitude may be kept constant and the pacing pulse width may be decreased by one step decrement at block 408. For the sake of illustration, the threshold test described in conjunction with FIG. 7 is performed by decreasing the pacing pulse amplitude while keeping the pacing pulse width constant. However it is recognized that the threshold test may be performed by decreasing the pulse width given a fixed pulse amplitude, or a combination of pulse amplitude decrements and pulse width decrements may be used. Furthermore, while the threshold test is described as starting at a high pulse amplitude that is decreased in a stepwise manner, it is recognized that the threshold test may be performed by starting with a low pulse amplitude and increasing the pulse amplitude until the different types of capture are each identified, or a binary or other search algorithm may be used to adjust the His bundle pacing pulse energy to determine each of the His bundle capture threshold and the VM capture threshold.

Control circuit 80 determines if NSHB capture is still occurring at block 410 after the first decrease in the pacing pulse amplitude. If NSHB is detected at block 410, the pacing pulse energy continues to be decreased, e.g., by decreasing the pulse amplitude, until NSHB capture is no longer detected. If NSHB capture is no longer detected, the NSHB capture threshold is determined at block 411 as the lowest, preceding pacing pulse amplitude at which NSHB capture was detected. The His bundle pacing pulse at the current test amplitude and pulse width, at which NSHB capture was lost, may be capturing only the His bundle (SHB capture) or capturing only ventricular myocardial tissue (VM capture) but is no longer capturing both.

At block 412, control circuit 80 analyzes the His bundle near field signal and/or the far field cardiac electrical signal to determine if criteria for detecting SHB capture are satisfied or if criteria for detecting VM capture are satisfied after NSHB capture is no longer detected. Control circuit 80 may monitor the His bundle near field signal at block 410 and determine that NSHB capture is no longer occurring in response to detecting a near field evoked response signal that is later than the SHB time interval threshold and/or switched from being a negative polarity signal to a positive polarity signal. Based on the later near field evoked response signal and/or positive polarity evoked response signal indicating SHB capture, NSHB capture is no longer detected at block 410, and SHB capture is detected at block 414 ("no" branch of block 412). The NSHB capture threshold determined at block 411 is also reported as the VM capture threshold at bock 416 since VM capture was lost when NSHB capture was lost, leaving only SHB capture.

However, if a conversion from NSHB capture to SHB capture is not determined at block 412 based on analysis of the near field signal, control circuit 80 may analyze the far field signal to detect a loss of NSHB capture due to loss of His bundle capture, leading to VM capture. In another example, since NSHB capture was initially determined at block 406, control circuit 80 may monitor only the far field cardiac electrical signal at block 410 with each step decrease in His bundle pacing pulse amplitude to detect a loss in NSHB capture based on a change in the far field evoked response signal. For instance, if the far field evoked response signal becomes later in time following the His bundle pacing pulse or increases in signal width and/or area, control circuit 80 may determine that NSHB capture is no longer occurring at block 410. If the far field evoked response signal is still occurring early after the His bundle pacing pulse but is wider and/or increased in area, NSHB capture is not detected at block 410, and VM capture is detected at block 412.

In order to positively detect VM capture at block 412, control circuit 80 may compare the far field evoked response signal width and/or area to respective width and area thresholds set to predetermined values to distinguish VM capture from NSHB capture. If the far field evoked response signal is later in time at block 410, neither NSHB capture nor VM capture is detected at respective blocks 410 and 412. Control circuit 80 may perform additional analysis of the near field signal at block 414 to positively detect SHB capture based on criteria relating to the timing, polarity, width and/or area of the near field evoked response signal.

Capture of the His bundle is lost if VM capture is detected at block 412 after losing NSHB capture at block 410. The most recent His bundle pacing pulse amplitude and width that resulted in NSHB capture at block 410 is therefore the His bundle capture threshold. At block 428, control circuit 80 may report the His bundle capture threshold by storing the His bundle capture threshold in memory 82 and/or transmitting the His bundle capture threshold via telemetry circuit 88 for display on external device 50.

Control circuit 80 may advance to block 432 to control therapy delivery circuit 84 to decrease the His bundle pacing pulse amplitude until VM capture is lost at block 434. The lowest pacing pulse amplitude for the fixed pacing pulse width at which VM capture was still detected at block 434 is reported as the VM capture threshold at block 436.

In this case, a pacing pulse amplitude set to a value that is greater than or equal to the His bundle capture threshold results in NSHB pacing. A pacing pulse amplitude that is less than the His bundle capture threshold results in ventricular myocardial pacing. SHB capture may not be achievable without repositioning of the selected pacing electrode vector since the VM capture threshold is less than the His bundle capture threshold. The His bundle capture threshold is equal to the NSHB capture threshold in this situation of the His bundle capture threshold being greater than the VM capture threshold. If the His bundle capture threshold is not unacceptably high, NSHB pacing may be desired over ventricular myocardial pacing to provide conduction along the native conduction pathway. Furthermore, during NSHB pacing, even if His bundle capture is lost due to a change in the His bundle capture threshold, VM capture may still be achieved to ensure that the patient does not experience ventricular asystole.

If VM capture is not detected after losing NSHB capture at block 410, SHB capture is detected at block 414. In this case, capture of the ventricular myocardial tissue is lost first as the pacing pulse amplitude is decreased. The VM capture threshold may be reported at block 416 as the lowest pulse amplitude at which NSHB capture was still detected, e.g., by storing the VM capture threshold in memory 82 and/or transmitting the VM capture threshold to external device 50. Control circuit 80 continues to control the therapy delivery circuit 84 to decrease the His bundle pacing pulse energy at block 418 until SHB capture is no longer detected at block 420. The His bundle capture threshold is the lowest pulse amplitude at which SHB capture was still detected. The His bundle capture threshold is reported at block 428. In this situation, SHB capture is achievable if the pacing pulse amplitude is set to be equal to or greater than the His bundle capture threshold but less than the VM capture threshold. NSHB capture may be desired, however, in order to reduce the likelihood of ventricular asystole. As such, the pacing pulse amplitude may be set higher than the VM capture threshold to promote NSHB pacing.

In some patients, depending on the local anatomy, electrode positioning or other factors, NSHB capture may not be detected in response to delivering the maximum pulse energy test pacing pulse at block 406. If SHB capture is detected following the first test pacing pulse at block 422, the highest pulse energy tested is below the VM capture threshold. The selected pacing electrode vector may be positioned such that only the His bundle is captured. Control circuit 80 may decrease the pacing pulse energy at block 424 until SHB capture is no longer detected at block 426, e.g., based on monitoring only the near field evoked response signal. At block 428, the His bundle capture threshold is reported as the lowest pulse amplitude at which SHB capture was still detected. In this case, the threshold search is complete since VM capture was never detected, so there is no VM capture threshold to determine and report.

If NSHB capture is not detected in response to the first, highest pacing pulse amplitude at block 406, VM capture may be detected at block 430 based on any of the example analyses of the His bundle near field and/or far field signals described above. If VM capture is detected at block 430, His bundle capture may not be achieved without relocating the His bundle pacing electrode vector. The pulse amplitude may be decreased at block 432 until VM capture is lost at block 434. The VM capture threshold amplitude may be reported at block 436 as the lowest pacing pulse amplitude at which VM capture was still detected. The determined and reported His bundle capture threshold, VM capture threshold and NSHB capture threshold corresponding to the higher one of the His bundle capture threshold and the VM capture threshold may be used by a clinician or by control circuit 80 to select a pacing pulse amplitude to achieve a desired type of capture.

Figure 8:
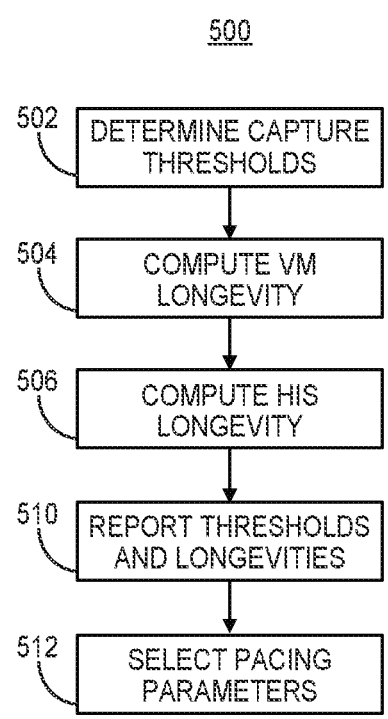
FIG. 8 is a flow chart of a method for determining IMD battery longevity and recommended pacing parameters based on His bundle capture threshold test results.

FIG. 8 is a flow chart 500 of a method for determining an expected IMD battery longevity and recommended pacing parameters based on His bundle capture threshold test results. At block 502, control circuit 80 may determine the His bundle capture threshold and the VM capture threshold using the techniques of FIG. 7. When both of the VM capture threshold and the His bundle capture threshold are determined, the higher one of the two is also the NSHB capture threshold. In some examples, the NSBH and VM capture types may not be distinguished.

At block 504, the expected battery longevity of the pacing device (e.g., IMD 14 or pacemaker 100) is computed based on pacing at, or a safety margin above, the VM capture threshold. The control circuit 80 may compute the expected battery longevity taking into account the remaining battery charge, an expected pacing burden based on historical data from the patient, the pacing pulse amplitude set to a programmed safety margin above the VM capture threshold, the programmed pacing pulse width and other pacing control parameters. At block 506, the expected battery longevity of the pacing device is determined by control circuit 80 based on pacing at a safety margin above the His bundle capture threshold.

At block 510, the capture thresholds and the expected battery longevity for pacing at a safety margin above the VM capture threshold and the expected battery longevity for pacing at a safety margin above the His bundle capture threshold are reported, e.g., by displaying the results on external device 50. The processor 52 of external device 50 may receive the determined capture thresholds and corresponding predicted battery longevities and generate a tabular, graphical, or textual display of the data. If the VM capture threshold is greater than the His bundle capture threshold, the device longevity for pacing at or above the VM capture threshold may correspond to the expected battery longevity if NSHB pacing is provided and is shorter than the expected battery longevity for SHB pacing. If the His bundle capture threshold is greater than the VM capture threshold, expected battery longevity for providing NSHB pacing may be less than providing VM only pacing. As such, in order to achieve NSHB pacing, the expected useful life of the pacing device may be shortened.

In some cases, NSHB pacing is desired to provide conduction of the evoked response along the normal conduction pathway with the assurance that if His bundle capture is lost VM capture may still occur. If the NSHB capture threshold (which may be equal to either the His bundle capture threshold or the VM capture, whichever is greater) is too high, the expected battery longevity of the pacing device may become unacceptably short. In the case of the VM capture being higher, the potential benefit of His bundle pacing with the assurance of backup VM capture in the case of losing His bundle capture may not outweigh the shortened functional lifetime of the pacing device. In this case, SHB pacing using a pulse amplitude that is less than the NSHB capture threshold may be preferred.

In the case of the His bundle capture threshold being greater than the VM capture threshold, ventricular pacing may be provided at a lower pacing pulse amplitude. VM pacing may be preferred in order to achieve a longer useful life of the pacing device when the SHB and corresponding NSHB capture threshold are substantially higher.

At block 512, the control circuit 80 (or external device 50) may select pacing parameters based on the capture thresholds and the corresponding expected battery longevities. In some examples, selected pacing parameters may be reported as recommended pacing parameters that are displayed on the external device 50. Display unit 54 of external device 50 may be used to display graphical user interface (GUI) generated by processor 52 that enables recommended pacing parameters and the associated capture thresholds and expected battery longevities to be displayed to a user and enable the user to accept a recommended setting such as pacing pulse amplitude or reject the recommended setting and select a different setting.

In other examples, the selected pacing parameters are automatically selected at block 512 by control circuit 80 for use in controlling therapy delivery circuit 84. Control circuit 80 may select the pacing parameters at block 512 by comparing the NSHB capture threshold (equal to either the His bundle capture threshold or the VM capture threshold, whichever is greater when both are determined) to a maximum pulse amplitude limit. If the NSHB capture threshold is less than the maximum limit (or the associated battery longevity is greater than a minimum battery longevity limit), the pacing pulse amplitude may be selected to be a safety margin above the NSHB capture threshold. His bundle pacing is provided with the assurance that VM capture is still provided if His bundle capture is lost.

If the His bundle capture threshold is less than the VM capture threshold, the pacing pulse amplitude may be selected at block 512 to be greater than the His bundle capture threshold but less than the VM capture threshold. SHB pacing may be provided using a lower pulse energy to conserve battery charge and provide the benefits of pacing the ventricles via the native conduction system.

Figure 9:
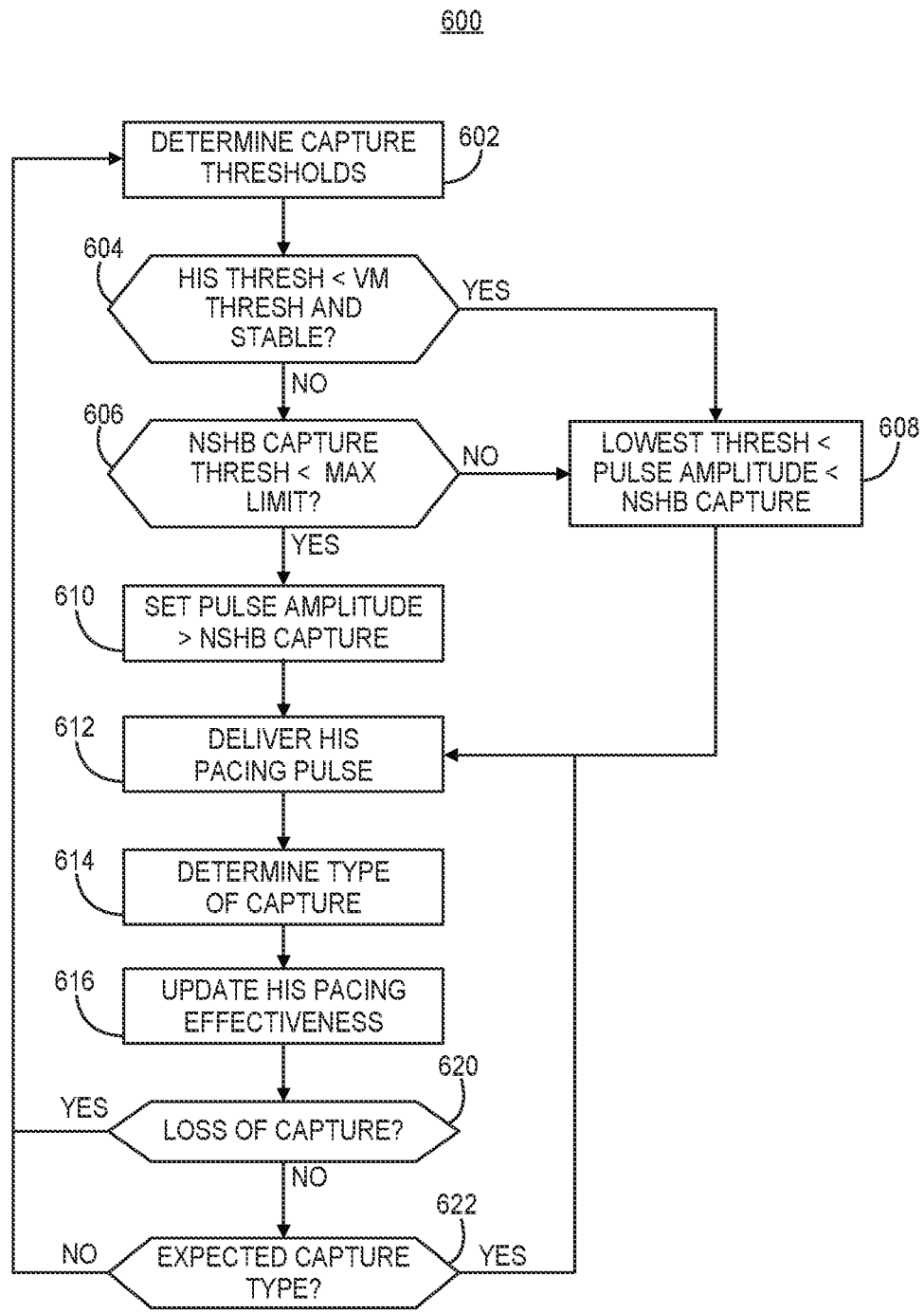
FIG. 9 is a flow chart of a method for capture monitoring during His bundle pacing according to one example.

FIG. 9 is a flow chart 600 of a method for capture monitoring during His bundle pacing according to one example. At block 602, the control circuit 80 may perform a capture threshold test to determine the His bundle capture threshold, the VM capture threshold, and the NSHB capture threshold equal to the greater one of the two. The capture threshold determination at block 602 may include any of the His bundle pacing capture determination techniques disclosed herein, e.g., the method described in conjunction with FIG. 7 above and/or including the method described in conjunction with FIG. 12 using atrial retrograde conduction timing determination. Control circuit 80 may determine whether the His bundle capture threshold is less than the VM capture threshold at block 602 and whether the His bundle capture threshold has been stable for one or more threshold tests. During a recovery period after initial implantation of the IMD system, inflammation and healing at the His bundle pacing electrode vector site may cause fluctuation in the capture thresholds. During an acute phase after surgery, NSHB pacing may be desired to provide His bundle pacing with the assurance that ventricular myocardial capture will occur if His bundle capture is lost. If the SHB capture threshold is stable and less than the VM capture threshold, however, SHB pacing may be desired to pace the ventricles via the native conduction system and conserve battery charge. As such, the type of pacing delivered (NSHB pacing, VM only pacing or SHB pacing) may be selected based on the capture thresholds, the stability of the His bundle capture threshold and taking into account the expected battery longevity of the IMD.

Control circuit 80 may determine that the His bundle capture threshold is stable based on a comparison of the current His bundle capture threshold to one or more previous His bundle capture thresholds. For example, if the His bundle capture threshold has not increased more than the programmed safety margin since the last capture threshold test (or a running average of two or more previously determined His bundle capture thresholds), the His bundle capture threshold may be determined to be stable. If the His bundle capture threshold is stable and less than the VM capture threshold, the control circuit 80 may set the pacing pulse amplitude at block 608 to a safety margin, e.g., 0.25 to 0.5 Volts, greater than the lower His bundle capture threshold but less than the NSHB capture threshold (equal to the higher VM capture threshold in this case). SHB pacing is provided at block 612 using a pacing pulse amplitude set based on the low, stable His bundle capture threshold.

If the His bundle capture threshold is greater than the VM capture threshold or unstable, however, NSHB pacing may be desired to promote VM capture if His bundle capture is lost. Accordingly, at block 606, control circuit 80 may compare the NSHB capture threshold to a maximum limit. An upper limit may be set to prevent excessive battery drain in the case of the NSHB capture threshold being unacceptably high. The maximum limit of the NSHB capture threshold may be set based on a minimum acceptable predicted battery longevity of the IMD. If the NSHB capture threshold is greater than the maximum limit, control circuit 80 may set the pacing pulse amplitude to a value less than the NSHB capture threshold at block 608. The pacing pulse amplitude may be set to a safety margin above the lower one of the His bundle capture threshold and the VM capture threshold. When the lower threshold is the His bundle capture threshold, a higher safety margin may be used to set the pacing pulse amplitude at block 608 to account for instability of the His bundle capture threshold. For example, the pacing pulse amplitude may be set to a multiple of the programmed safety margin if the His bundle capture threshold has been found to increase by more than the safety margin since the last capture threshold test. The multiple of the safety margin may be set based on how much the His bundle capture threshold has increased since a previous capture threshold test without causing the pulse amplitude to exceed the NSHB capture threshold (or other maximum pulse amplitude limit).

If the VM capture threshold is lower than the His bundle capture threshold at block 604 and the NSHB capture threshold is greater than a maximum limit at block 606, the pacing pulse amplitude may be set to a safety margin above the VM capture threshold and less than the NSHB (and His bundle) capture threshold at block 608. Ventricular myocardial pacing may be delivered until the His bundle capture threshold is lower and/or more stable. VM pacing is provided at block 612 using a pacing pulse amplitude set based on the VM bundle capture threshold.

If the His bundle capture threshold is greater than the VM capture threshold, or is instable but the NSHB capture threshold is less than the maximum limit (as determined at blocks 604 and 606), control circuit 80 may set the pacing pulse amplitude to a safety margin greater than the NSHB capture threshold at block 610. NSHB pacing may be desired until the His bundle threshold is lower than the VM threshold and is stable. In this case, the pacing pulse amplitude is set to a safety margin greater than the NSHB capture threshold at block 610. Providing NSHB pacing provides the assurance of VM capture when the His bundle capture is instable and/or higher than the VM capture threshold.

After setting the pacing pulse amplitude at block 608 or 610 to deliver the selected type of pacing (VM, SHB, or NSHB pacing) based on the determined capture thresholds, His pacing pulses are delivered at block 612 using the selected pacing pulse amplitude. At bock 614, control circuit 80 monitors His bundle pacing capture by determining the type of capture following a His bundle pacing pulse. Capture may be determined on a beat-by-beat basis, every n pacing pulses, once per minute, once per hour, once per day or other scheduled basis. Capture determination may additionally occur on a triggered basis in response to a particular event or other sensor signal. The type of capture is determined at block 614 as one of at least SHB capture, NSHB capture or VM capture using the methods described above in conjunction with FIG. 5 and/or methods described below in conjunction with FIGS. 11 and 12. In some instances, loss of capture may be determined at block 614 due to the pacing pulse amplitude falling below both the His bundle capture threshold and the VM capture threshold. In other examples, capture monitoring may include detecting other types of capture or events as described above in conjunction with FIG. 6.

After determining the type of capture (or loss of capture) at block 614, control circuit 80 may update a log stored in memory 82 at block 616 that counts how often each type of capture is detected to provide a metric of effective His bundle pacing. The percentage or number of times that NSHB capture is detected, SHB capture is detected, and VM capture is detected (and optionally other types of capture or events) may be tracked and updated each time the type of capture is determined. This data may be transmitted to external device 50. Processor 52 may generate a display of the data for viewing by a clinician on display unit 54. Knowledge of the percentage of time that the His bundle is successfully being captured as opposed to only ventricular myocardial pacing may provide useful diagnostic or prognostic information that is helpful in selecting pacing therapy parameters.

If loss of capture is detected, as determined at block 620, control circuit 80 may perform another capture threshold test by returning to block 602. If the type of capture that is expected is detected at block 622, control circuit 80 continues to deliver His pacing pulses according to the currently selected pacing control parameters (block 612) and monitoring capture (block 614) according to the capture monitoring protocol. The expected type of capture is based on the type of pacing and pacing pulse amplitude selected at block 608 or 610. For example, if the pacing pulse amplitude was set greater than the NSHB capture threshold, NSHB capture is expected. If the pacing pulse amplitude was set to be less than the NSHB capture threshold, then SHB capture or VM capture is expected, depending on which was found to have the lower capture threshold during the most recent capture threshold test.

If the type of capture detected is not the expected type of capture ("no" branch of block 622), one or both of the VM capture threshold and the His bundle capture threshold may have changed. Control circuit 80 may perform a new capture threshold test by returning to block 602. Based on the new capture threshold test results, the pacing pulse amplitude may be set differently to achieve a different type of capture. In this way, His bundle pacing is provided when the His bundle capture threshold is below a maximum acceptable limit (or the corresponding battery longevity is at least a minimum acceptable limit). Ventricular myocardial pacing is provided when the His bundle capture threshold is unacceptably high. NSHB pacing may be provided when the SHB capture threshold is higher than the VM capture threshold and/or instable but less than the maximum capture threshold limit.

Figure 10:
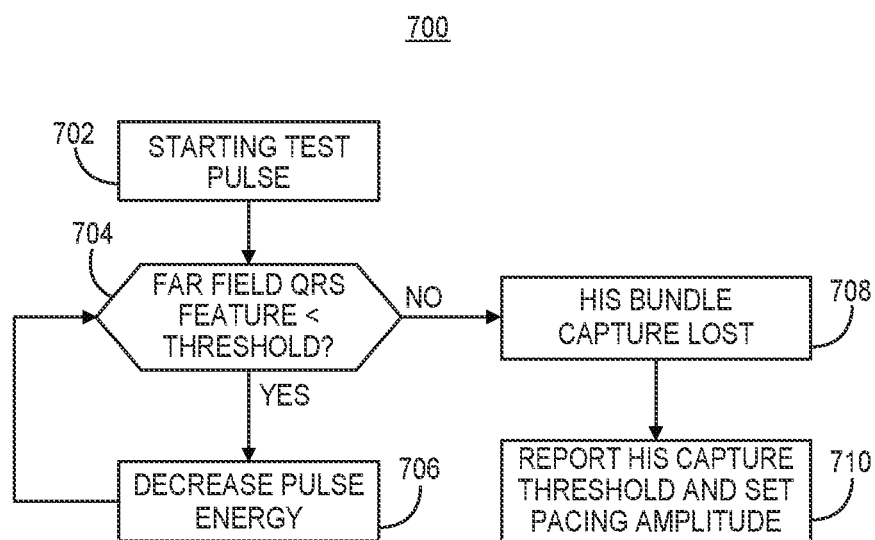
FIG. 10 is a flow chart of a method for performing a capture threshold test for His bundle pacing according to another example.

FIG. 10 is a flow chart 700 of a method for determining His bundle capture threshold according to another example. At block 702, a His bundle pacing pulse is delivered at a starting pulse energy using electrodes positioned for His bundle pacing. The starting pulse energy is set to be well above the expected His bundle capture threshold to promote a high likelihood of capturing the His bundle on the first test pulse.

At block 704, control circuit 80 determines a feature of the QRS signal from the far field cardiac electrical signal, such as the QRS width and/or QRS area. The determined feature is compared to a threshold at block 704 to determine if the far field QRS width and/or area are less than a threshold width and/or threshold area, respectively. If so, the relatively narrow QRS and/or small QRS area indicates that the His bundle is being captured, whether the capture type is SHB or NSHB capture. The control circuit 80 controls therapy delivery circuit 84 to decrease the His bundle pacing pulse energy at block 706, e.g., by reducing the pulse amplitude by a predetermined decrement. His pacing at the reduced pulse energy is delivered at block 704. This process continues until the far field QRS feature determined after a His pacing pulse delivered at a reduced pulse energy is greater than the threshold at block 704. If the far field QRS feature is greater than the threshold at block 704 ("no" branch), His capture is lost (block 708). A widening of the far field QRS signal and/or increased far field QRS signal area indicates that VM capture is occurring without capture of the His bundle.

At block 710 the His bundle capture threshold may be reported as the lowest pacing pulse energy applied before losing His bundle capture. Control circuit 80 may automatically set the His bundle pacing pulse energy at block 710 to a safety margin greater than the His bundle capture threshold. Additionally or alternatively, the control circuit 80 may report the His bundle capture threshold to a clinician by transmitting the capture threshold to external device 50 for display. In some clinical applications, pacing the His bundle is acceptable whether selective capture or non-selective capture of the His bundle is occurring. As such, discriminating only between VM capture and capture that includes His bundle capture, which may be either SHB or NSHB capture, is all that may be required for selecting a pacing pulse control parameters to promote His bundle pacing.

Figure 11:
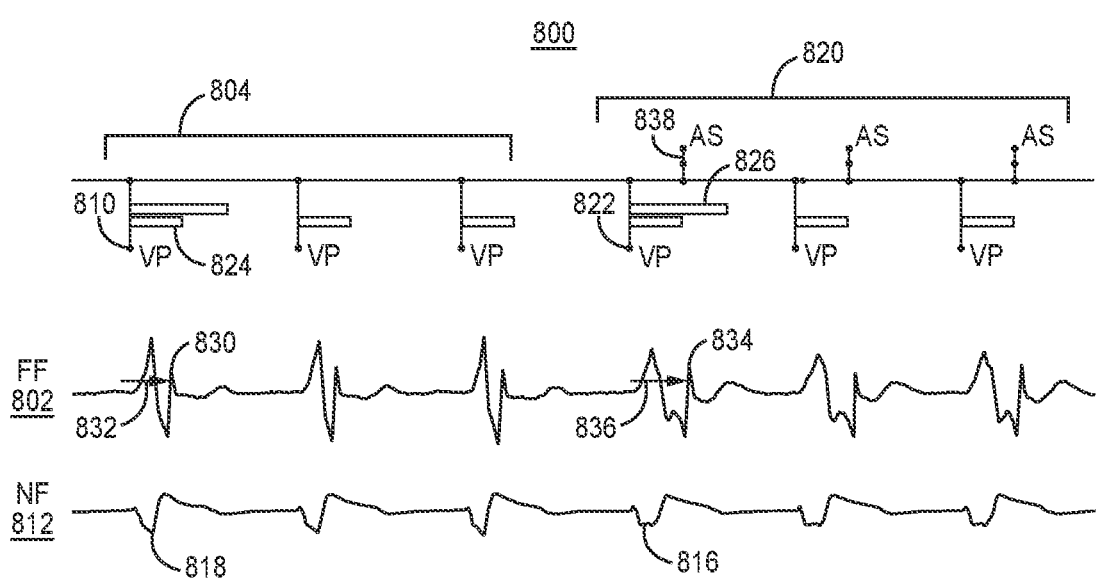
FIG. 11 is a diagram of evoked response signals during His bundle pacing in a non-atrial tracking pacing mode.

FIG. 11 is a diagram 800 of evoked response signals during His bundle pacing in a non-atrial tracking pacing mode. In the example of FIG. 11, three His bundle pacing pulses are delivered at a first pacing pulse amplitude that produces His bundle capture 804 starting with the first pacing pulse 810. His bundle capture 804 is NSHB capture in the example shown. The next three His bundle pacing pulses starting with pacing pulse 822 are delivered at a second pacing pulse amplitude that is less than the first pacing pulse amplitude and less than the His bundle capture threshold resulting in VM capture 820.

The near field His bundle signal 812 includes R-waves 818 that are relatively narrow during NSHB capture 804 and R-waves 816 that are relatively wider during VM capture 820. This difference in QRS width in the near field His bundle signal 812 may or may not be discriminating between NSHB and VM capture. The far field cardiac electrical signal 802 includes evoked atrial P-waves 830 and 834 during NSHB capture 804 and VM capture 820, respectively. These evoked atrial P-waves 830 and 834 occur during the non-atrial tracking pacing mode, e.g., a VDI pacing mode. The atria may be in a non-refractory state when the His bundle pacing pulses 810 and 822 are delivered asynchronously with the atrial events (intrinsic P-waves and/or atrial pacing pulses). Retrograde conduction of an evoked depolarization of the His bundle results in an early, retrograde-conducted, evoked P-wave 830 during NSHB capture 804. The evoked P-wave 830 occurs at a retrograde conduction time 832 following the His bundle pacing pulse 810.

During VM capture 820, loss of His bundle capture results in a different retrograde conduction pathway from the ventricular myocardium to the atrial myocardium that may not involve retrograde conduction along the His bundle. The retrograde conduction of a depolarization wavefront through the ventricular myocardium produces evoked atrial P-wave 834 at a relatively longer retrograde conduction time 836 from the delivered His bundle pacing pulse 822 (that fails to capture the His bundle) than the retrograde conduction time 832 following His bundle capture. This longer retrograde conduction time 836 during VM capture 820 compared to the retrograde conduction time 832 during NSHB capture 804 may be determined and used by control circuit 80 for discriminating between NSHB capture (or SHB capture) and VM capture.

The change in retrograde conduction time may be determined during a non-atrial tracking pacing mode. During an atrial tracking pacing mode, such as DDD or VDD, the His bundle pacing pulse may be delivered at an AV pacing interval following an intrinsic atrial P-wave or an atrial pacing pulse, during the physiological refractory period of the atrial myocardium such that no retrograde conduction occurs. As such, in order to determine changes in the retrograde conduction time, such as the change between time intervals 832 and 836, following a His pacing pulse delivered via a His pacing electrode vector, control circuit 80 may be configured to control the therapy delivery circuit 84 to deliver one or more His bundle pacing pulses asynchronously with the atrial events to promote retrograde conduction of a depolarization wavefront and the occurrence of an evoked P-wave following the His bundle pacing pulse.

Control circuit 80 may be configured to control sensing circuit 86 to set a post-ventricular atrial blanking (PVAB) period 824 upon delivering each of the His bundle pacing pulses 810 and 822. The PVAB period 824 may be applied to avoid false sensing of far-field R-waves as an atrial P-wave. During NSHB capture 804, the relatively short retrograde conduction time 832 following capture of the His bundle may produce an evoked P-wave 830 during the PVAB period 824 such that no atrial sensed event signal is produced by sensing circuit 86. The evoked P-wave 834 during VM capture, however, may occur after the PVAB period 824, after the relatively long retrograde conduction time 836. As a result, the sensing circuit 86 may produce an atrial sensed event signal 838 in response to the far field signal 802 crossing a P-wave sensing threshold outside the PVAB period 824. Control circuit 80 may be configured to detect VM capture and loss of His bundle capture in response to detecting an increase in retrograde conduction time and/or in response to the timing of atrial sensed event signals 838 received from sensing circuit 86 after His bundle pacing pulses 822 during a non-atrial tracking ventricular pacing mode.

In other examples, control circuit 80 may be configured to shorten the PVAB period 824 to enable sensing of retrograde-conducted evoked P-waves 830 during His bundle capture 804 as well as during VM capture 820. Determination of the relative timing of sensed atrial P-waves, e.g., early or relatively later after a His bundle pacing pulse that is delivered asynchronously with atrial events, may be used for determining the type of capture of the His bundle pacing pulse.

Control circuit 80 may be configured to set a post-ventricular atrial refractory period (PVARP) 826 to facilitate determination of the timing of atrial sensed event signals relative to a His bundle pacing pulse and subsequently the type of capture of the His bundle pacing pulse. For instance, PVARP 826 may be set to expire at a maximum myocardial retrograde conduction time interval. A refractory sensed atrial P-wave 838 sensed after PVAB 824 but before expiration of PVARP 826 indicates retrograde conduction of a His bundle pacing pulse that captured the ventricular myocardium but did not capture the His bundle. An atrial sensed event signal received by control circuit 80 after PVARP 826 may be indicative of a supraventricular intrinsic P-wave that is not conducted retrograde from the His bundle pacing site. In various examples, therefore, PVAB period 824 and PVARP 826 may be set based on the expected minimum and maximum retrograde conduction time following capture of the His bundle and/or the expected minimum and maximum retrograde conduction time following capture of the ventricular myocardium and loss of His bundle capture. In this way, control circuit 80 may determine the timing of sensed atrial events relative to a His bundle pacing pulse for discriminating between different types of capture of the His bundle pacing pulse. In other examples, a timer or counter may be implemented in control circuit 80 to determine the time interval from a delivered His bundle pacing pulse to a sensed P-wave following the His bundle pacing pulse, e.g., time interval 832 or 836, and compare the time interval to a time interval threshold or range that distinguishes between His bundle capture with retrograde conduction and VM capture with retrograde conduction.

In some instances, retrograde conduction could occur after His bundle capture, and retrograde block could occur with VM capture because the atrial myocardium may be in a state of refractoriness. Accordingly, the timing of a P-wave sensed event signal that is early after the His bundle pacing pulse may be evidence of His bundle capture. The absence of a P-wave sensed event signal after a His pacing pulse may be an indication of VM capture, or more generally a loss of His bundle capture.

Figure 12:
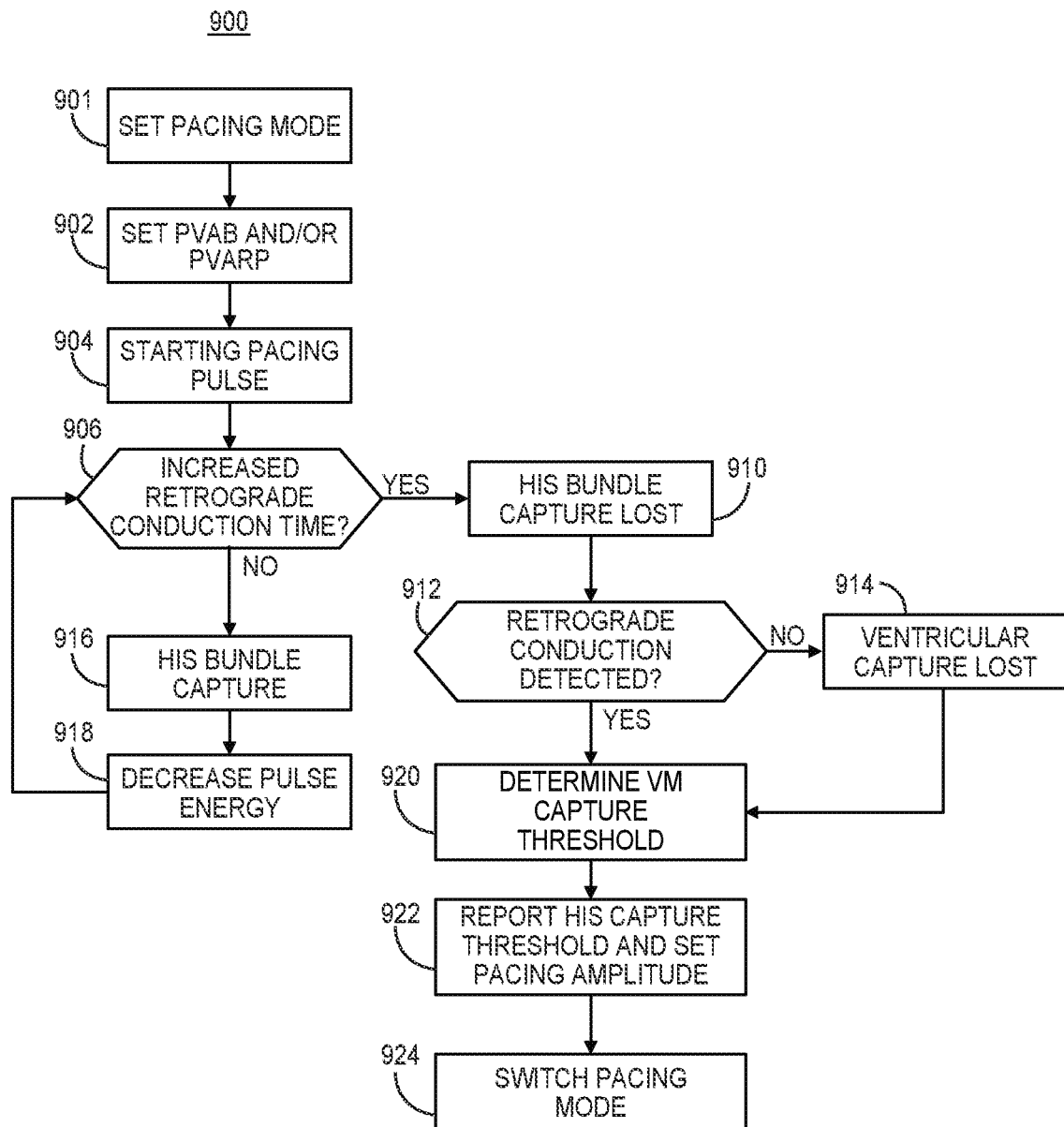
FIG. 12 is a flow chart of a method for detecting His bundle loss of capture using a timing of a sensed P-wave according to one example.

FIG. 12 is a flow chart 900 of a method for determining the type of capture following a His bundle pacing pulse according to one example. In some examples, control circuit 80 may be configured to perform a capture threshold test using retrograde conduction time as a discriminator between His bundle capture and VM capture. Control circuit 80 may normally be controlling therapy delivery circuit 84 to pace the ventricles in an atrial tracking ventricular pacing mode, e.g., DDD or VDD pacing. The control circuit 80 may perform a capture threshold test periodically, e.g., on a scheduled basis, or in response to a triggering event, e.g., loss of His bundle capture detected based on an increased QRS area, QRS width, or change in QRS waveform morphology. A template comparison to an unknown QRS waveform may be used to determine the capture type during His pacing capture monitoring. In some cases, changes in QRS area, width or morphology due to loss of His bundle capture may be difficult to discriminate with high confidence. A capture threshold test or capture verification based on retrograde conduction time, or the timing of atrial sensed events, may increase the confidence in a His Bundle capture determination based on QRS area, width and/or QRS waveform morphology. In some examples, the timing of atrial sensed events following His bundle pacing pulses may be used instead of or in combination with QRS area, QRS width, QRS polarity, overall waveform morphology or other features of the QRS signal as described above in conjunction with FIGS. 4 and 5 for detecting and discriminating between capture types.

At block 901, control circuit 80 may set the pacing mode to a non-atrial tracking ventricular pacing mode so that therapy delivery circuit 84 is controlled to deliver His bundle pacing pulses at a selected ventricular rate, independent of the rate or occurrence of atrial sensed or paced events. The non-atrial tracking ventricular pacing mode includes atrial sensing, such as a VDI mode, in order to enable control circuit 80 to detect retrograde conducted atrial P-waves. An AV pacing interval is not triggered in response to sensed P-waves in the pacing mode set at block 901. For example, the pacing mode may be switched to a temporary VDI pacing mode from normal operation in a DDD or VDD mode, which provides atrial synchronized His bundle pacing that tracks the atrial rate.

Control circuit 80 may optionally set a PVAB and/or a PVARP at block 902 according to test settings used for determining the timing of atrial sensed events relative to the preceding delivered His bundle pacing pulse for detecting His bundle loss of capture. In some examples, the PVAB period may be set to a minimum myocardial retrograde conduction time threshold indicative of VM capture. An atrial sensed event signal received by control circuit 80 from sensing circuit 86 after expiration of the PVAB is indicative of loss of His bundle capture and may be indicative of VM capture. In other examples, the PVAB period may be shortened to a minimal period, e.g., 20 or 30 ms, to enable sensing of retrograde conducted P-waves during both His bundle capture and VM capture so that a change in the timing of the sensed P-waves after His bundle pacing pulses can be detected. For example, by determining an increase in the retrograde conduction time from a short time interval to a longer time interval, as shown in FIG. 11, control circuit 80 may detect His bundle loss of capture.

In still other examples, the PVAB period may be set to a minimal period, e.g., 20 or 30 ms, at block 902, and the PVARP may be set to a maximum His bundle retrograde conduction time threshold indicative of His bundle capture. A refractory atrial event sensed during the PVARP indicates His bundle capture and a non-refractory atrial event sensed after the PVARP expires is evidence of loss of His bundle capture. If the non-refractory atrial event is sensed within a maximum myocardial retrograde conduction time limit, the non-refractory atrial sensed event is evidence VM capture. As such, in various examples, control circuit 80 may be configured to set the PVAB period and/or PVARP at block 902 based on minimum and/or maximum retrograde conduction time interval thresholds corresponding to retrograde conduction involving the His bundle and/or corresponding to retrograde conduction via the myocardium and not involving the His bundle. Atrial sensed event signals within or outside the PVAB period and/or within or outside the PVARP can then be used for detecting and discriminating between His bundle capture and VM capture based on the timing of the atrial P-waves.

At block 904, a starting pacing pulse is delivered at a selected VV pacing interval following a most recently preceding His bundle pacing pulse or sensed R-wave. The starting pacing pulse is set to a starting pulse amplitude, which may be a maximum amplitude or other relatively high amplitude that is expected to capture the His bundle. In other examples, the starting pulse may be set to the most recently determined His bundle capture threshold or to a safety margin greater than the most recently determined His bundle capture threshold. In other examples, the starting pacing pulse amplitude may be set to the current pacing pulse amplitude to determine if pacing at the current pulse amplitude is capturing the His bundle.

At block 906, control circuit 80 determines if the next sensed atrial event following the starting His bundle pacing pulse occurs at a retrograde conduction time that is relatively long (e.g., greater than an established maximum His bundle retrograde conduction threshold) or is increased compared to a previously determined retrograde conduction time. In some examples, the determination made at block 906 may be based on determining the timing of an atrial sensed event signal received from sensing circuit 86 by using the PVAB period and/or PVARP. For example, the PVAB period may be set at block 902 to a maximum retrograde conduction time threshold indicative of His bundle capture (or conversely a minimum myocardial retrograde conduction time threshold that is indicative of VM capture). If an atrial event is sensed after the PVAB period, an increased retrograde conduction time may be detected at block 906. The relatively long retrograde conduction time is indicative of retrograde conduction via myocardial tissue rather than the His bundle.

In other examples, increased retrograde conduction time is detected at block 906 in response to the next sensed atrial event signal occurring after the PVAB period and before expiration of a retrograde conduction time maximum threshold. A PVARP may be set to a maximum expected retrograde conduction time. A refractory sensed atrial event may indicate a retrograde-conducted atrial event that is conducted via the myocardium in this case and is an indication of His bundle loss of capture.

In other examples, increased retrograde conduction time may be detected at block 906 by control circuit 80 by determining the retrograde conduction time interval from the starting pacing pulse delivered at block 904 to a subsequently sensed atrial P-wave. For example, the PVAB period may be set very short to enable sensing of early evoked P-waves due to retrograde conduction of a His bundle depolarization wavefront and relatively later evoked P-waves due to retrograde conduction of a ventricular myocardial depolarization wavefront. Control circuit 80 may compare the determined retrograde conduction time interval to a threshold time interval at block 906. If the time interval is greater than the threshold, His bundle loss of capture is detected at block 910. If the retrograde conduction time interval is less than the threshold time interval, control circuit 80 detects His bundle capture at block 916 (which may be SHB capture or NSHB capture). Control circuit 80 may decrease the pulse energy at block 918 and return to block 906 to search for the His bundle capture threshold based on a detection of increased retrograde conduction time.

In some examples, a single pacing pulse delivered at block 904 may lead to a determination that His bundle capture is lost at block 910 due to detection of increased retrograde conduction time at block 906. In this case, while not shown explicitly in FIG. 12, it is to be understood that control circuit 80 may increase the pacing pulse amplitude and return to block 906 to begin a search for the His bundle capture threshold.

In some examples, after determining that His bundle capture is lost, control circuit 80 may determine whether retrograde conduction is detected at all at block 912. An atrial sensed event signal may be received from sensing circuit 86 later than a maximum retrograde conduction time limit. The atrial sensed event signal later than the maximum retrograde conduction time limit is an indication of an intrinsic, supraventricular P-wave with no retrograde conduction. In this case, both His bundle and VM loss of capture may have occurred such that ventricular capture is lost entirely, as determined at block 914. The VM capture threshold may be higher than the His bundle capture threshold, and therefore VM capture may be lost at a higher pacing pulse amplitude than the pacing pulse amplitude at which His bundle capture is lost. In examples that include setting a PVARP to a maximum myocardial refractory conduction time limit, a non-refractory sensed atrial event may indicate ventricular loss of capture.

If retrograde conduction is not detected at all, indicating ventricular loss of capture at block 914, or if His bundle capture is lost (block 910) but retrograde conduction is still detected at block 912 ("yes" branch), additional steps in pacing pulse amplitude adjustments may be performed at block 920 for optionally determining the VM capture threshold based on the timing of atrial sensed events or retrograde conduction time intervals. For instance, His bundle capture is lost when the relative timing of atrial sensed event signals or retrograde conduction time interval changes from being within a maximum expected His bundle retrograde conduction time limit to being after the maximum expected His bundle retrograde conduction time limit. VM capture is lost when atrial sensed event signals or retrograde conduction time interval changes from being between minimum and maximum VM retrograde conduction time limits to being later than the maximum VM retrograde conduction time or earlier than the minimum VM retrograde conduction time limit. Ventricular capture is lost when the atrial sensed event signals are later than a maximum VM retrograde conduction time limit indicating no retrograde conduction.

After determining at least the His bundle capture threshold based on atrial sensed event timing relative to the PVAB period and/or PVARP and/or determined retrograde conduction time interval(s) from a His bundle pacing pulse, control circuit 80 may report the His bundle capture threshold at block 922 and/or set the His bundle pacing pulse amplitude to a safety margin above the His bundle capture threshold. If the VM capture threshold is determined at block 920, the VM capture threshold may also be reported at block 922. Control circuit 80 may make a recommendation or a selection of the pacing pulse amplitude for providing NSHB (greater than the higher one of the SHB and VM capture thresholds) or SHB pacing (greater than the SHB capture threshold but less than the VM capture threshold), which may take into account IMD battery longevity as described previously herein. At block 924, control circuit 80 may switch the pacing mode back to a permanent pacing mode, such as VDD or DDD, which allows atrial synchronized His bundle pacing to be resumed at a pacing amplitude sufficient to capture the His bundle.

Figure 13:
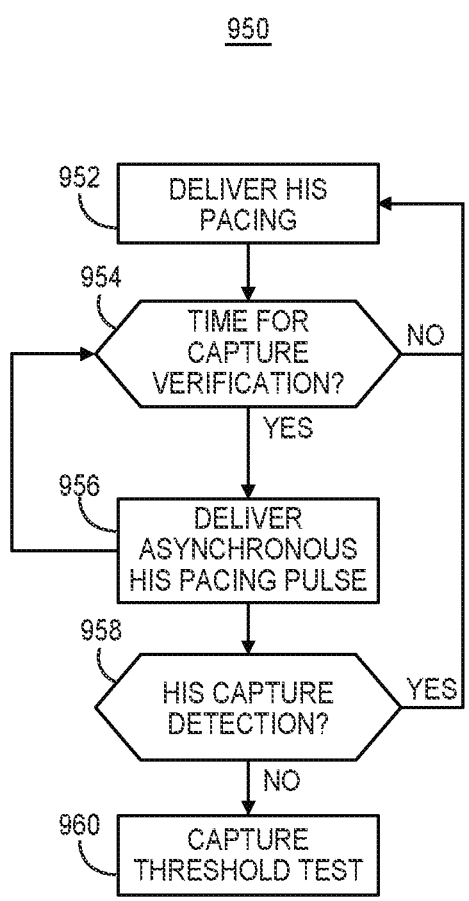
FIG. 13 is a flow chart of a method for detecting His bundle loss of capture according to another example.

FIG. 13 is a flow chart 950 of a method for monitoring His bundle capture according to another example. At block 952, therapy delivery circuit 84 may be delivering His bundle pacing under the control of control circuit 80 according to a programmed atrial tracking ventricular pacing mode, e.g., DDD or VDD. At block 954, control circuit 80 may determine that it is time to verify His bundle capture. His bundle capture verification based on retrograde conduction time may be performed periodically, e.g., once per minute, once per hour, etc. or on every nth His bundle pacing pulse. At block 956, control circuit 80 controls the therapy delivery circuit 84 to deliver a His bundle pacing pulse asynchronously with atrial events. For example, the His bundle pacing pulse may be delivered at a test VV pacing interval or at a very long AV pacing interval so that the His bundle pacing pulse is delivered while the atrial myocardium is not in a state of physiological refractoriness.

At block 958, control circuit 80 determines if the His bundle is captured by detecting an atrial sensed event signal received from sensing circuit 86 and determining if the timing of the atrial sensed event signal indicates retrograde conduction involving the His bundle. Any of the techniques described above may be used by control circuit 80 for determining if His bundle capture is detected. For instance, control circuit 80 may determine a time interval from the asynchronous pacing pulse to the next atrial sensed event signal and compare the time interval to a maximum retrograde conduction time interval corresponding to retrograde conduction involving the His bundle (either SHB or NSHB capture). Alternatively, control circuit 80 may set a very short PVAB period and set the PVARP equal to the maximum retrograde conduction time expected when His bundle capture occurs. A refractory atrial sensed event signal (after PVAB period and during PVARP) is indicative of His bundle capture.

If His bundle capture is detected at block 958, the process returns to block 952 to continue delivering His bundle pacing pulses according to the currently programmed pacing mode, e.g., DDD or VDD, without adjusting pacing pulse control parameters. If His bundle capture is not detected at block 958, based on the timing of the next atrial sensed event following the asynchronous His pacing pulse, control circuit 80 may perform a His bundle capture threshold search at block 960. The His bundle capture threshold search may be performed according to the capture threshold determination techniques disclosed herein, such as the methods described in conjunction with FIGS. 5-7 or FIG. 12 or any combination thereof.

According to the techniques described in conjunction with FIGS. 11, 12 and 13, detection of His bundle capture or loss of capture may be based only on the timing of atrial sensed events following His bundle pacing pulses that are delivered asynchronously to atrial events. It is to be understood, however, that the timing of atrial sensed events as an indication of retrograde conduction time and the type of cardiac capture achieved by a His bundle pacing pulse may be used by control circuit 80 in any combination with the R-wave polarity, QRS width, QRS area, or QRS waveform morphology of the near field or far field cardiac electrical signal for determining the type of ventricular capture (including any of SHB capture, NSHB capture, VM capture, and/or loss of ventricular capture among other possible events as listed in TABLE I above). Furthermore, it is recognized that the techniques for determining His bundle and/or VM capture threshold based at least in part on determining the timing of refractory conducted atrial sensed events may be used in combination with the other capture detection, capture threshold determination, and pacing pulse amplitude selection techniques disclosed herein and described in conjunction with any of the flow charts of FIGS. 5-10 and 12-13.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of circuits or components associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, an 1 MB has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. An implantable medical device system, comprising:
   a sensing circuit configured to sense a first cardiac electrical signal via a first sensing electrode vector;
   a therapy delivery circuit configured to generate pacing pulses; and
   a control circuit configured to determine a type of cardiac capture evoked by a first pacing pulse generated by the therapy delivery circuit by:
      detecting from the first cardiac electrical signal a QRS signal following the first pacing pulse;
      determining a time interval from the first pacing pulse to the QRS signal;
      determining that the time interval from the first pacing pulse to the QRS signal is greater than a first threshold time interval and less than a second threshold time interval; and
      determining the type of cardiac capture to be selective capture of the ventricular conduction system without myocardial capture based on the determined time interval being greater than the first threshold time interval and less than the second threshold time interval.

2. The medical device of claim 1, wherein the control circuit is further configured to determine the type of cardiac capture by:
   determining that a polarity of the QRS signal is positive; and
   determining that the type of cardiac capture is selective capture of the ventricular conduction system without myocardial capture based on the polarity of the QRS signal being positive and the determined time interval being greater than the first threshold time interval and less than the second threshold time interval.

3. The medical device of claim 1, wherein:
   the sensing circuit is configured to sense a second cardiac electrical signal via a second sensing electrode vector different than the first sensing electrode vector; and
   the control circuit is further configured to determine the type of cardiac capture by:
      determining a QRS signal feature from the second cardiac electrical signal;
      determining that the QRS signal feature meets ventricular conduction system capture criteria; and
      determining that the type of cardiac capture is capture of the ventricular conduction system without myocardial capture based on the QRS signal feature of the second cardiac electrical signal meeting the ventricular conduction system capture criteria and the determined time interval being greater than the first threshold time interval and less than the second threshold time interval.

4. The medical device of claim 3, wherein the control circuit is configured to:
determine the QRS signal feature by determining a QRS signal width; and
determine that the QRS signal feature meets the ventricular conduction system capture criteria by determining that the QRS signal width is less than a threshold width.

5. The medical device of claim 1, wherein the control circuit is further configured to determine a type of cardiac capture evoked by a second pacing pulse generated by the therapy delivery circuit by:
determining from the first cardiac electrical signal a second time interval from the second pacing pulse to a subsequent QRS signal of the first cardiac electrical signal;
determining that the second time interval is less than the first threshold time interval; and
determining that the type of cardiac capture evoked by the second pacing pulse includes ventricular myocardial capture based on the second time interval being less than the first threshold time interval.

6. The medical device of claim 5, wherein:
the sensing circuit is configured to receive a second cardiac electrical signal via a second sensing electrode vector different than the first sensing electrode vector;
the control circuit is further configured to determine that the type of cardiac capture evoked by the second pacing pulse includes ventricular myocardial capture by:
determining a QRS signal feature from the second cardiac electrical signal;
determining that the QRS signal feature meets ventricular myocardial capture criteria; and
determining that the type of cardiac capture is ventricular myocardial capture without ventricular conduction system capture based on the QRS signal feature meeting the ventricular myocardial capture criteria and the determined time interval being less than the first threshold time interval.

7. The medical device of claim 5, wherein:
the sensing circuit is configured to receive a second cardiac electrical signal via a second sensing electrode vector different than the first sensing electrode vector;
the control circuit is further configured to determine that the type of cardiac capture evoked by the second pacing pulse includes ventricular myocardial capture by:
determining a QRS signal feature from the second cardiac electrical signal;
determining that the QRS signal feature meets non-selective ventricular conduction system capture criteria; and
determining that the type of cardiac capture evoked by the second pacing pulse includes ventricular conduction system capture and ventricular myocardial capture based on the QRS signal feature meeting the non-selective ventricular conduction system capture criteria and the determined time interval being less than the first threshold time interval.

8. The medical device of claim 6, wherein:
the therapy delivery circuit is configured to:
generate the first pacing pulse having a first pulse energy; and
generate the second pacing pulse having a second pulse energy different than the first pulse energy; and the control circuit is configured to set a pacing pulse energy used by the therapy delivery circuit to generate subsequent cardiac pacing pulses based on the second pulse energy.

9. The medical device of claim 5, wherein:
the therapy delivery circuit is configured to:
generate the first pacing pulse having a first pulse energy; and
generate the second pacing pulse having a second pulse energy greater than the first pulse energy; and
the control circuit is configured to set a pacing pulse energy used by the therapy delivery circuit to generate subsequent cardiac pacing pulses based on the first pulse energy.

10. The medical device of claim 1, further comprising a memory,
wherein the control circuit is further configured to:
determine a type of cardiac capture evoked by each of a plurality of the pacing pulses generated by the therapy delivery circuit;
determine a percentage of the determined types of cardiac capture of each of the plurality of pacing pulses that include ventricular conduction system capture; and
generate an output of the percentage of the determined types of cardiac capture that include ventricular conduction system capture; and
wherein the memory is configured to store the output.

11. A method, comprising:
sensing a first cardiac electrical signal;
generating pacing pulses; and
determining a type of cardiac capture evoked by a first pacing pulse of the generated pacing pulses by:
detecting from the first cardiac electrical signal a QRS signal following the first pacing pulse;
determining a time interval from the first pacing pulse to the QRS signal;
determining that the time interval from the first pacing pulse to the QRS signal is greater than a first threshold time interval and less than a second threshold time interval; and
determining the type of cardiac capture to be selective capture of the ventricular conduction system without myocardial capture based on the determined time interval being greater than the first threshold time interval and less than the second threshold time interval.

12. The method of claim 11, wherein determining the type of cardiac capture further comprises:
determining that a polarity of the QRS signal is positive; and
determining that the type of cardiac capture is selective capture of the ventricular conduction system without myocardial capture based on the polarity of the QRS signal being positive and the determined time interval being greater than the first threshold time interval and less than the second threshold time interval.

13. The method of claim 11, further comprising:
sensing a second cardiac electrical signal different than the first cardiac electrical signal;
determining a QRS signal feature from the second cardiac electrical signal;
determining that the QRS signal feature meets ventricular conduction system capture criteria; and
determining that the type of cardiac capture is selective capture of the ventricular conduction system without myocardial capture based on the QRS signal feature of the second cardiac electrical signal meeting the ventricular conduction system capture criteria and the determined time interval being greater than the first threshold time interval and less than the second threshold time interval.

14. The method of claim 13, further comprising:
determining the QRS signal feature by determining a QRS signal width; and
determining that the QRS signal feature meets the ventricular conduction system capture criteria by determining that the QRS signal width is less than a threshold width.

15. The method of claim 11, further comprising:
determining from the first cardiac electrical signal a second time interval from a second pacing pulse to a subsequent QRS signal of the first cardiac electrical signal;
determining that the second time interval is less than the first threshold time interval; and
determining that a type of cardiac capture evoked by the second pacing pulse includes ventricular myocardial capture based on the second time interval being less than the first threshold time interval.

16. The method of claim 15, further comprising:
sensing a second cardiac electrical signal different than the first cardiac electrical signal;
determining a QRS signal feature from the second cardiac electrical signal;
determining that the QRS signal feature meets ventricular myocardial capture criteria; and
determining that the type of cardiac capture is ventricular myocardial capture without ventricular conduction system capture based on the QRS signal feature meeting the ventricular myocardial capture criteria and the determined time interval being less than the first threshold time interval.

17. The method of claim 15, further comprising:
sensing a second cardiac electrical signal different than the first cardiac electrical signal;
determining a QRS signal feature from the second cardiac electrical signal;
determining that the QRS signal feature meets non-selective ventricular conduction system capture criteria; and
determining that the type of cardiac capture evoked by the second pacing pulse includes ventricular conduction system capture and ventricular myocardial capture based on the QRS signal feature meeting the non-selective ventricular conduction system capture criteria and the determined time interval being less than the first threshold time interval.

18. The method of claim 16, further comprising:
generating the first pacing pulse having a first pulse energy;
generating the second pacing pulse having a second pulse energy different than the first pulse energy;
setting a pacing pulse energy based on the second pulse energy; and
generating subsequent cardiac pacing pulses at the pacing pulse energy.

19. The method of claim 15, further comprising:
generating the first pacing pulse having a first pulse energy;
generating the second pacing pulse having a second pulse energy greater than the first pulse energy;
setting a pacing pulse energy based on the first pulse energy; and
generating subsequent cardiac pacing pulses at the pacing pulse energy.

20. The method of claim 11, further comprising:
determining a type of cardiac capture evoked by each of a plurality of the generated pacing pulses;
determining a percentage of the determined types of cardiac capture that include ventricular conduction system capture; and
generating an output of the percentage of the determined types of cardiac capture that include ventricular conduction system capture.

21. A non-transitory, computer-readable medium storing a set of instructions which, when executed by a control circuit of a medical device, cause the medical device to:
sense a cardiac electrical signal;
generate a pacing pulse;
detect from the cardiac electrical signal a QRS signal following the pacing pulse;
determine a time interval from the pacing pulse to the QRS signal;
determine that the time interval from the pacing pulse to the QRS signal is greater than a first threshold time interval and less than a second threshold time interval; and
determine a type of cardiac capture by the pacing pulse to be selective capture of the ventricular conduction system without myocardial capture based on the determined time interval being greater than the first threshold time interval and less than the second threshold time interval.

* * * * *